United States Patent [19]
Burri et al.

[11] Patent Number: 5,292,740
[45] Date of Patent: Mar. 8, 1994

[54] SULFONAMIDES

[75] Inventors: Kaspar Burri, Binningen, Switzerland; Martine Clozel, St. Louis, France; Walter Fischli, Allschwil, Switzerland; Georges Hirth, Huningue, France; Bernd-Michael Löffler, Oberrimsingen, Fed. Rep. of Germany; Werner Neidhart, Bartenheim, France; Henri Ramuz, Birsfelden, Switzerland

[73] Assignee: Hoffmann-La Roche Inc., Nutley, N.J.

[21] Appl. No.: 896,015

[22] Filed: Jun. 9, 1992

[30] Foreign Application Priority Data

Jun. 13, 1991 [CH] Switzerland ................. 1760/91
May 12, 1992 [CH] Switzerland ................. 1516/92

[51] Int. Cl.$^5$ .............. C07D 403/04; C07D 413/04; C07D 401/14; C07D 403/14; C07D 239/47; C07D 239/48; C07D 401/04; A61K 31/505

[52] U.S. Cl. .............................. 514/256; 544/82; 544/296; 544/238; 544/295; 544/122; 544/123; 544/284; 544/270; 544/277; 544/310; 544/311; 544/317; 544/319; 544/320; 544/321; 544/325; 544/324; 544/327; 514/232.2; 514/235.8; 514/269; 514/272; 514/252; 514/274; 514/265; 514/275; 514/266; 514/262; 514/259

[58] Field of Search ............. 544/310, 311, 317, 319, 544/320, 321, 325, 324, 327, 82, 238, 122, 284, 277; 514/256, 269, 272, 274, 275, 262

[56] References Cited

U.S. PATENT DOCUMENTS 3,317,536  5/1967  Grussner et al. ............. 260/256.5

FOREIGN PATENT DOCUMENTS 1545944  5/1965  Fed. Rep. of Germany.

Primary Examiner—John M. Ford
Attorney, Agent, or Firm—George M. Gould; George W. Johnston; Ellen Ciambrone Coletti

[57] ABSTRACT

The novel sulfonamides of formula I,

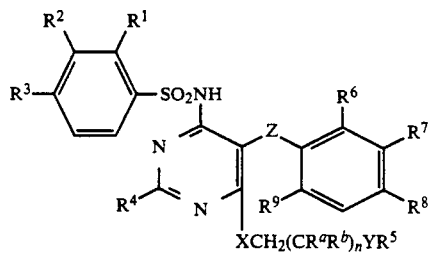

in which the symbols $R^1$-$R^9$, $R^a$, $R^b$, X, Y and n have the significance given in the description and salts thereof can be used for the treatment of circulatory disorders, especially hypertension, ischemia, vasopasms and angina pectoris.

33 Claims, No Drawings

SULFONAMIDES

SUMMARY OF THE INVENTION

The present invention relates to sulfonamides of the formula

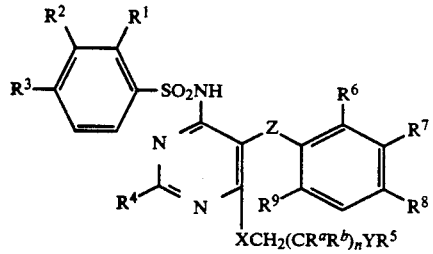

wherein

R$^1$ is hydrogen, lower-alkyl, lower-alkoxy, lower-alkylthio, halogen or trifluoromethyl;

R$^2$ is hydrogen, halogen, lower-alkoxy, trifluoromethyl or —OCH$_2$COOR$^a$; and R$^3$ is hydrogen, halogen, lower-alkyl, lower-alkylthio, trifluoromethyl, cycloalkyl, lower-alkoxy or trifluoromethoxy; or R$^2$ and R$^3$ together signify butadienyl, methylenedioxy, ethylenedioxy or isopropylidenedioxy;

R$^4$ is hydrogen, lower-alkyl, cycloalkyl, trifluoromethyl, lower-alkoxy, lower-alkylthio, lower-alkylthio-lower-alkyl, hydroxy-lower-alkyl, hydroxy-lower-alkoxy, lower-alkoxy-lower-alkyl, hydroxy-lower-alkoxy-lower-alkyl, hydroxy-lower-alkoxy-lower-alkoxy, lower-alkylsulphinyl, lower-alkylsulphonyl, 2-methoxy-3-hydroxypropoxy, 2-hydroxy-3-phenylpropyl, amino-lower-alkyl, lower-alkylamino-lower-alkyl, di-lower-alkylamino-lower-alkyl, amino, lower-alkylamino, di-lower-alkylamino, arylamino, aryl, arylthio, aryloxy, aryl-lower-alkyl or heterocyclyl;

R$^5$ is hydrogen, lower-alkyl, lower-alkanoyl, benzoyl, heterocyclylcarbonyl, heterocyclylmethyl or tetrahydropyran-2-yl;

R$^6$ to R$^9$ are hydrogen, halogen, trifluoromethyl, lower-alkyl, lower-alkoxy, lower-alkylthio, hydroxy, hydroxymethyl, cyano, carboxyl, formyl, methylsulphinyl, methylsulphonyl, methylsulphonyloxy or lower-alkyloxy-carbonyloxy; or R$^7$ together with R$^6$ or R$^8$ signify butadienyl, methylenedioxy, ethylenedioxy or isopropylidenedioxy;

Z is —O—, —S—, ethylene, vinylene, —CO—, —OCHR$^{10}$— or —SCHR$^{10}$;

R$^{10}$ is hydrogen or lower-alkyl;

X and Y each independently signify O, S or NH; or YR$^5$ also is lower-alkylsulphinyl or —OCH$_2$CH(OR$^c$)CH$_2$OR$^d$;

R$^a$, R$^b$, R$^c$ and R$^d$ each independently are hydrogen or lower-alkyl; or R$^c$ and R$^d$ together signify methylene, ethylene or isopropylidene; and n is 1, 2 or 3, and salts thereof.

DETAILED DESCRIPTION OF THE INVENTION

The present invention relates to sulfonamides of the formula

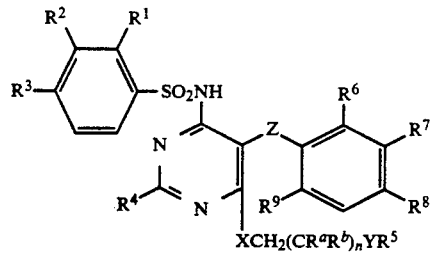

wherein

R$^1$ is hydrogen, lower-alkyl, lower-alkoxy, lower-alkylthio, halogen or trifluoromethyl;

R$^2$ is hydrogen, halogen, lower-alkoxy, trifluoromethyl or —OCH$_2$COOR$^a$; and R$^3$ is hydrogen, halogen, lower-alkyl, lower-alkylthio, trifluoromethyl, cycloalkyl, lower-alkoxy or trifluoromethoxy; or R$^2$ and R$^3$ together signify butadienyl, methylenedioxy, ethylenedioxy or isopropylidenedioxy;

R$^4$ is hydrogen, lower-alkyl, cycloalkyl, trifluoromethyl, lower-alkoxy, lower-alkylthio, lower-alkylthio-lower-alkyl, hydroxy-lower-alkyl, hydroxy-lower-alkoxy, lower-alkoxy-lower-alkyl, hydroxy-lower-alkoxy-lower-alkyl, hydroxy-lower-alkoxy-lower-alkoxy, lower-alkylsulphinyl, lower-alkylsulphonyl, 2-methoxy-3-hydroxypropoxy, 2-hydroxy-3-phenylpropyl, amino-lower-alkyl, lower-alkylamino-lower-alkyl, di-lower-alkylamino-lower-alkyl, amino, lower-alkylamino, di-lower-alkylamino, arylamino, aryl, arylthio, aryloxy, aryl-lower-alkyl or heterocyclyl;

R$^5$ is hydrogen, lower-alkyl, lower-alkanoyl, benzoyl, heterocyclylcarbonyl, heterocyclylmethyl or tetrahydropyran-2-yl;

R$^6$ to R$^9$ are hydrogen, halogen, trifluoromethyl, lower-alkyl, lower-alkoxy, lower-alkylthio, hydroxy, hydroxymethyl, cyano, carboxyl, formyl, methylsulphinyl, methylsulphonyl, methylsulphonyloxy or lower-alkyloxy-carbonyloxy; or R$^7$ together with R$^6$ or R$^8$ signify butadienyl, methylenedioxy, ethylenedioxy or isopropylidenedioxy;

Z is —O—, —S—, ethylene, vinylene, —CO—, —OCHR$^{10}$— or —SCHR$^{10}$;

R$^{10}$ is hydrogen or lower-alkyl;

X and Y each independently signify O, S or NH; or YR$^5$ also is lower-alkylsulphinyl or —OCH$_2$CH(OR$^c$)CH$_2$OR$^d$;

R$^a$, R$^b$, R$^c$ and R$^d$ each independently are hydrogen or lower-alkyl; or R$^c$ and R$^d$ together signify methylene, ethylene or isopropylidene; and n is 1, 2 or 3, and salts thereof.

The term "lower", as used herein, denotes groups with 1-7 C atoms, preferably 1-4 C atoms. Alkyl, alkoxy and alkylthio groups as well as alkyl groups as components of alkanoyl groups can be straight-chain or branched. Methyl, ethyl, propyl, isopropyl, butyl, sec. and tert.butyl are examples of such alkyl groups. Halogen denotes fluorine, chlorine, bromine and iodine, with chlorine being preferred. Cycloalkyl denotes residues with 3 to 8 C atoms, such as cyclopropyl, cyclobutyl, cyclopentyl or cyclohexyl, and the like. Examples of aryl residues are phenyl and substituted phenyl residues, with halogen, lower-alkyl, lower-alkoxycarboxyl and trifluoromethyl especially coming into consideration as substituents. Examples of heterocyclyl residues are especially substituted, for example, by lower alkyl, lower alkoxy, halogen, aryl, aryl-lower alkyl mono- or disubstituted, or unsubstituted mono or bicyclic 5- and 6-membered heterocyclic residues with oxygen, nitrogen or sulphur as the hetero atom, such as, for example, 2- and 3-furyl, pyrimidinyl, 2-, 3- and 4-pyridyl and pyridyl N-oxide, 1,2- and 1,4-diazinyl, morpholino, 2-and 3-thienyl, isoxazolyl, oxazolyl, imidazolyl, pyrrolyl, benzofuranyl, benzothienyl, indolyl, purinyl, quinolyl, isoquinolyl, quinazolyl, and the like.

The compounds of formula I are inhibitors of endothelin receptors. They can accordingly be used for the treatment of disorders which are associated with endothelin activities, especially circulatory disorders such as hypertension, ischaemia, vasospasms and angina pectoris.

A preferred group of compounds of formula I are those in which Z is —O— and, furthermore, those in which $R^6$ is lower-alkoxy, especially methoxy, and $R^7$, $R^8$ and $R^9$ are hydrogen; or $R^6$ and $R^8$ are hydrogen, $R^7$ is lower-alkoxy, especially methoxy, and $R^9$ is halogen, especially chlorine.

$R^1$ and $R^2$ are preferably hydrogen. $R^3$ is preferably lower-alkyl or together with $R^2$ methylene-dioxy. $R^4$ is preferably hydrogen, 2-pyrimidinyl, 2- and 3-furyl, 2- and 3-thienyl, morpholino or p-methoxyphenyl. X is preferably oxygen. $YR^5$ is preferably hydroxy, lower-alkoxysulphinyl or furoyloxy.

The compounds of formula I can be prepared by a) reacting a compound of the formula

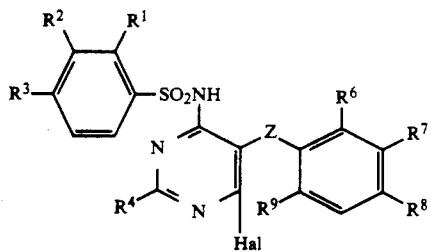

II wherein $R^1$, $R^2$, $R^3$, $R^4$ and $R^6$ have the significance given above and Hal is halogen, with a compound of the formula $$MX(CH_2)(CR^aR^b)_nYR^5 \quad \text{III}$$

wherein X, Y, n, $R^a$, $R^b$ and $R^5$ have the significance given above and M represents an alkali metal, or b) reacting a compound of the formula

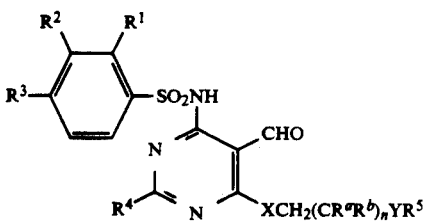

IV wherein $R^1$–$R^5$, $R^a$, $R^b$, X, Y and n have the significance given above, with a compound of the formula

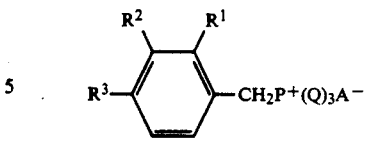

V wherein $R^6$–$R^8$ have the significance given above; Q is aryl and $A^-$ is an anion, or c) hydrogenating a compound of the formula

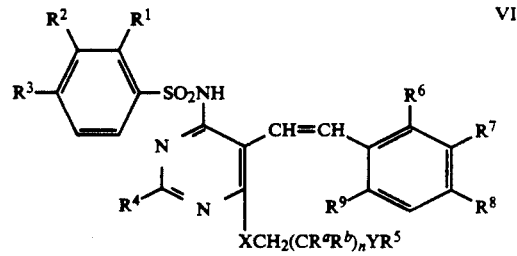

VI wherein $R^1$–$R^8$, $R^a$, $R^b$, X, Y and n have the significance given above, or d) reacting a compound of the formula

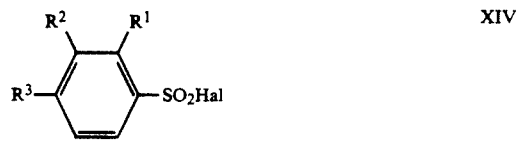

XIV with a compound of the formula

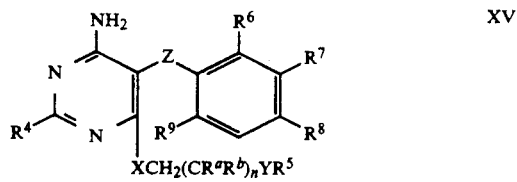

XV wherein $R^1$–$R^9$, $R^a$, $R^b$, X, Y, Z and n have the significance given above, and, if desired, modifying substituents present in the compound of formula I obtained and/or converting the compound of formula I obtained into a salt.

The reaction of a compound of formula II with a compound of formula III is conveniently carried out using the glycol corresponding to the compound III, for example, in ethylene glycol when n=2. The alkali metal M is preferably sodium. The reaction is conveniently carried out while heating, for example, to 40°–120° C. In a preferred embodiment, the monosodium salt of ethylene glycol, propylene glycol or butylene glycol is used as the compound of formula III.

The reaction of a compound of formula IV with a compound of formula V can be carried out in a known manner under the usual conditions of a Wittig reaction. The aryl residue Q is preferably phenyl; examples of anions $A^-$ are $Cl^-$, $Br^-$, $HSO_4^-$ and tosyloxy. The reaction partners are conveniently reacted with each other in the presence of an acid-binding agent, for example, in the presence of a strong base such as, for example, butyllithium, sodium hydride or the sodium salt of dimethyl sulphoxide, or K tert.-butylate, but preferably in the presence of an optionally lower alkyl-substituted ethylene oxide such as 1,2-butylene oxide, optionally in a solvent, for example, in an ether such as diethyl ether or tetrahydrofuran or in an aromatic hydrocarbon such as benzene, in a temperature range lying between room temperature and the boiling point of the reaction mixture. In the Wittig reaction, interfering reactive groups in the reaction partners, such as carboxyl or amino, are conveniently intermediately protected, for example, as a carboxylic acid ester or as the tert.butoxycarbonylamino derivative.

The hydrogenation of a compound of formula VI can be carried out in a known manner for the hydrogenation of olefinic double bonds, for example, with hydrogen at normal pressure or elevated pressure in the presence of noble metal catalysts such as Pd, especially Pd on carriers such as Pd/C.

Any hydroxy groups and an amino group that may be group, for example, the acetate, or such groups or ketals, which can be present, for example, as a substituent $YR^5$, contained in the initially obtained reaction product can be cleaved off in a known manner. Methylthio groups can be oxidized to methylsulphinyl or methylsulphonyl groups. Furthermore, N-heterocyclic residues such as pyridyl can be oxidized to N-oxides. All of these reactions can be carried out according to known methods. The compounds of formula I can be converted into salts, for example, alkali salts such as Na and K salts, in a known manner.

The compounds which are used as starting materials, insofar as they are not known or their preparation is described hereinafter, can be prepared in analogy to known methods or to the methods described hereinafter.

Compounds of formula II can be obtained as illustrated in the following Formula Scheme:

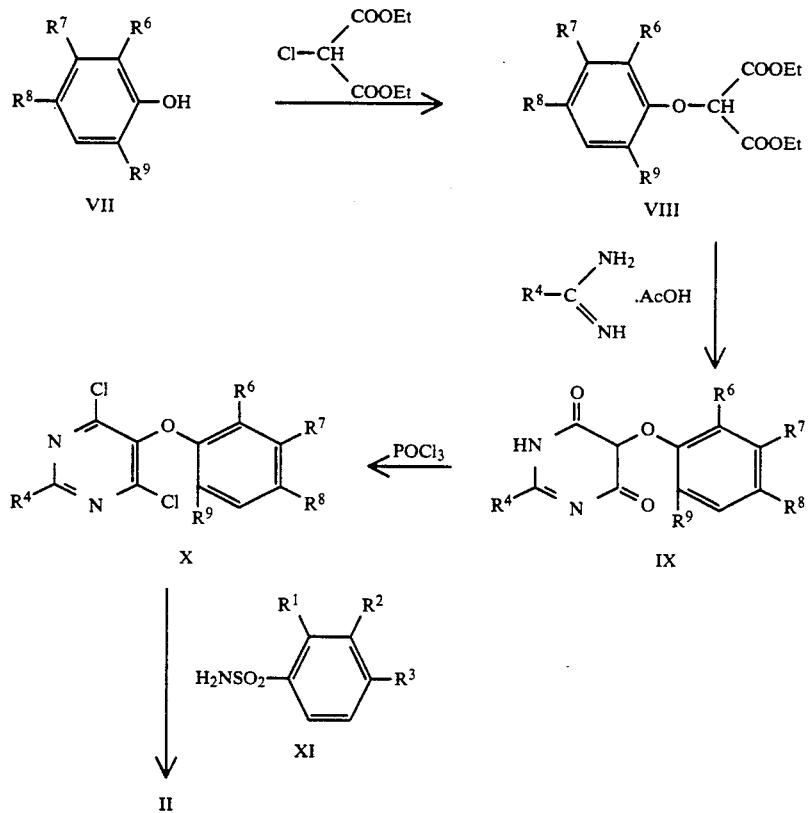

present in the substituent $R^4$ to $R^9$ of the compound of formula XV are suitably protected when reacting this compound. Hydroxy groups may be protected, for example, by silyl groups such as dimethyl t-butyl silyl, or acyl groups such as acetyl; and amino groups may be protected by t-butoxy carbonyl a benzyloxy carbonyl. These protecting groups can be inserted and, after the reaction of the compounds XIV and XV, be cleaved by known methods.

Substituents present in the thus-obtained compound of formula I can be modified. For example, a hydroxy group $YR^5$ can be esterified or etherified. A hydroxy group $YR^5$ can be converted into an ether group, for example, the tetrahydropyranyl ether, or an ester Alkylation of the phenol VII with diethyl chloromalonate yields compound VIII which is condensed with formamidine acetate or a homologous compound such as acetamidine acetate to the pyrimidinedione derivative IX. Using phosphorus oxychloride there is obtained therefrom the dichloro compound X which yields compound II upon reaction with a stoichiometric amount of compound XI. All of these reactions are standard operations and can be carried out under conditions which are usual for such reactions and which are familiar to a person skilled in the art.

Compounds of formula IV can be obtained according to the Reaction Scheme sketched hereinafter:

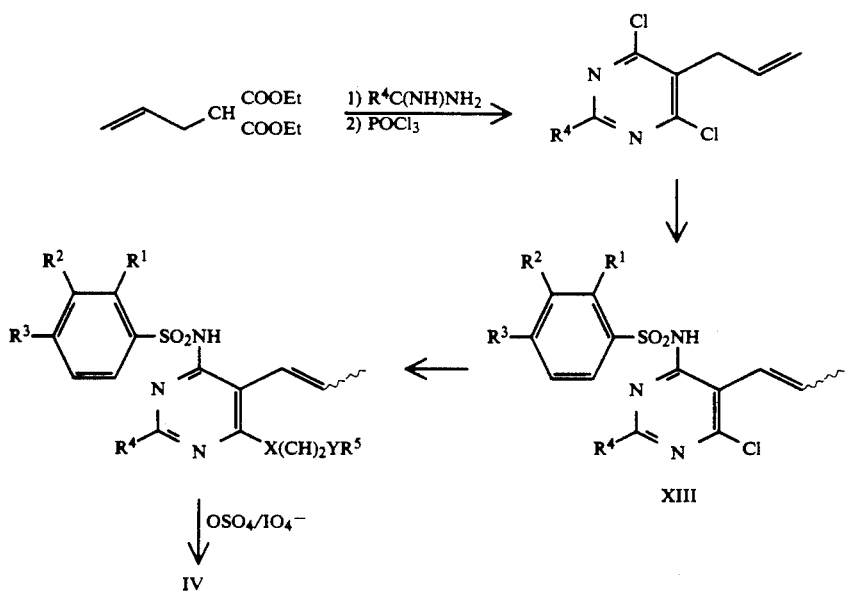

Condensation of diethyl allyl malonate with formamidine acetate or a $R^4$-substituted derivative followed by replacement of the hydroxy groups by chlorine in the pyrimidinedione obtained yields the dichloropyrimidine XII which is condensed with a $R^1$, $R^2$, $R^3$-benzenesulfonamide alkali salt with rearrangement of the allyl double bond to the compound XIII. Reaction of compound XIII with a compound III in the manner already described leads to compound XIV. Oxidative cleavage of the double bond of the propenyl side-chain in compound XIV finally yields the aldehyde IV.

The inhibitory activity of the compounds of formula I on endothelin receptors can be demonstrated using the test procedures described hereinafter:

I: Inhibition of endothelin binding to human placenta membranes (see. Life Sci 44:1429 (1989))

Human placenta is homogenized in 5 mM Tris buffer, pH 7.4, which contains 1 mM $MgCl_2$ and 250 mM sucrose. The homogenizate is centrifuged at 4° C. and 3000 g for 15 minutes, the supernatant containing the plasma membrane fraction is centrifuged with 72000 g for 30 minutes and the precipitate is washed with 75 mM Tris buffer, pH 7.4, which contains 25 mM $MgCl_2$. Thereafter, precipitate obtained from, in each case, 10 g of original tissue is suspended in 1 ml of 75 mM Tris buffer, pH 7.4, containing 25 mM $MgCl_2$ and 250 mM sucrose, and freeze-dried at −20° C. in 1 ml aliquots.

For the binding assay, the freeze-dried membrane preparations are thawed and, after centrifugation at 20° C. and 25000 g for 10 minutes, re-suspended in assay buffer (50 mM Tris buffer, pH 7.4, containing 25 mM $MnCl_2$, 1 mM EDTA and 0.5% of bovine serum albumin). 100 ml of this membrane suspension containing 70 mg of protein are incubated with 50 ml of $^{125}$I-endothelin (specific activity 2200 Ci/mMol) in assay buffer (25000 cpm, final concentration 20 pM) and 100 ml of assay buffer containing varying concentrations of test compound. The incubation is carried out at 20° C. for 2 hours or at 4° C. for 24 hours. The separation of free and membrane-bound radioligands is carried out by filtration over a glass fibre filter.

The inhibitory activity of compounds of formula I determined in this test procedure is given in Table 1 as the $IC_{50}$, that is, as the concentration [mM] which is required to inhibit 50% of the specific binding of $^{125}$I-endothelin.

TABLE 1

| Compound of Example | $IC_{50}$ [mM] |
|---|---|
| 1 | 0.115 |
| 2 | 0.100 |
| 6 | 0.200 |
| 12 | 0.125 |
| 24 | 0.073 |
| 25 | 0.050 |
| 27 | 0.099 |

II. Inhibition of endothelin-induced contractions in isolated rat aorta rings

Rings with a length of 5 mm were cut out from the thorax aorta of adult Wistar-Kyoto rats. The endothelium was removed by lightly rubbing the internal surface. Each ring was immersed at 37° C. in 10 ml of Krebs-Henseleit solution in an isolated bath while gassing with 95% $O_2$ and 5% $CO_2$. The isometric stretching of the rings was measured. The rings were stretched to a pretension of 3 g. After incubation for 10 minutes with the test compound or vehicle, cumulative dosages of endothelin-1 were added. The activity of the test compound was determined by calculating the dosage ratios, that is, the shift to the right (shift to higher values) of the $EC_{50}$ of endothelin induced by 100 mM of test compound, with $EC_{50}$ denoting the endothelin concentration required for a half-maximum contraction. The greater this dosage ratio is the more potent the test compound is in inhibiting the biological activity of endothelin-1. The $EC_{50}$ of endothelin in the absence of test compounds is 0.3 nM.

The thus-obtained values for the shift to the right of the $EC_{50}$ of endothelin with compounds of formula I are given in Table 2.

TABLE 2

| Compound of Example | Dosage ration (Shift to the right) |
|---|---|
| 1 | 165 |
| 6 | 395 |
| 24 | 257 |

TABLE 2-continued

| Compound of Example | Dosage ration (Shift to the right) |
| --- | --- |
| 25 | 238 |

III. The inhibitory activity of the compounds of formula I on vasoconstriction can be observed in vivo in rats in the test procedure described hereinafter:

Rats were anaesthetized with Na thiobutabarbital (100 mg/kg i.p.). A catheter for measuring the systemic arterial blood pressure was placed through the femoral artery and a catheter was placed in the vena cava via the femoral vein for injection of the test compounds. A Doppler sonde was placed around the left renal artery and attached to a Doppler measuring apparatus. A renal ischaemia was produced by pinching off the left renal artery at its point of exit for 45 minutes. 10 minutes prior to the induction of the ischaemia the test compounds were administered intraarterially (i.a.) in dosages of 5 mg/kg or intravenously (i.v.) in dosages of 10 mg/kg. In control tests, the renal perfusion was reduced by 43±4% compared to the preischaemic value.

The results obtained with two compounds of formula I are given in Table 3.

| Compound of Example | % Decrease in renal perfusion |
| --- | --- |
| 1 | 13.4 ± 5.2 |
| 6 | 11.7 ± 4.7 |

On the basis of their capability of inhibiting endothelin binding, the compounds of formula I can be used as medicaments for the treatment of disorders which are associated with vaso-constriction of increasing occurrences. Examples of such disorders are high blood pressure, coronary disorders, cardiac insufficiency, renal and myocardial ischaemia, renal insufficiency, dialysis, cerebral ischaemia, cardiac infarct, migraine, subarachnoid haemorrhage, Raynaud syndrome and pulmonary high pressure. They can also be used in atherosclerosis, the prevention of restenosis after balloon-induced vascular dilation, inflammations, gastric and duodenal ulcers, ulcus cruris, gram-negative sepsis, shock, glomerulonephtritis, renal colic, glaucoma, asthma, in the therapy and prophylaxis of diabetic complications and complications in the administration of cyclosporin, as well as other disorders associated with endothelin activities.

The compounds of formula I can be administered orally, rectally, parentally, for example, intravenously, intramuscularly, subcuta- neously, intrathecally or transdermally, or sublingually or as opththalmological preparations, or as an areosol. Capsules, tablets, suspensions or solutions for oral administration, suppositories, injection solutions, eye drops, salves or spray solutions are examples of application forms.

Intravenous, intramuscular or oral application is a preferred form of use. The dosages in which the compounds of formula I are administered in effective amounts depend on the nature of the specific active ingredient, the age and the requirements of the patient and the mode of application. In general, dosages of about 0.1-100 mg/kg body weight per day come into consideration. The preparations containing the compounds of formula I can contain inert or also pharmacodynamically active additives. Tablets or granulates, for example, can contain a series of binders, fillers, carriers or diluents. Liquid preparations can be present, for example, in the form of a sterile water-miscible solution. Capsules can contain a filler or thickener in addition to the active ingredient. Furthermore, flavor-improving additives, as well as, substances usually used as preserving, stabilizing, moisture-retaining and emulsifying agents as well as salts for varying the osmotic pressure, buffers and other additives can also be present.

The previously mentioned carrier materials and diluents can comprise organic or inorganic substances, for example, water, gelatin, lactose, starch, magnesium stearate, talc, gum arabic, polyalkylene glycols and the like. It is a prerequisite that all adjuvants used in the manufacture of the preparations are non-toxic.

The following Examples illustrate the invention in more detail. Of the abbreviations used therein THF signifies tetrahydrofuran; DMSO signifies dimethyl sulphoxide; MeOH signifies methanol; b.p. signifies boiling point; and m.p. signifies melting point.

EXAMPLE 1 a) 886 mg of p-t-butyl-N-[6-chloro-5-(o-methoxyphenoxy)-4-pyrimidinyl]benzenesulfonamide were added to a sodium glycolate solution from 3.0 g of ethylene glycol and 138 mg of sodium. The reaction mixture was stirred at 95° C. under argon for 4 hours. Thereafter, the ethylene glycol was distilled off and the residue was partitioned between ethyl acetate and 1N hydrochloric acid. The organic phase was dried and the solvent was distilled off. The residue was crystallized from diisopropyl ether. There were obtained 870 mg of p-t-butyl-N-[6-(2-hydroxyethoxy)-5-(o-methoxyphenoxy)-4-pyrimidinyl]benzenesulfonamide. M.p. 143°–148° C.

b) 775 mg of the previously obtained sulfonamide were dissolved in 20 ml of warm ethanol. The solution was treated with a stoichiometric amount of sodium ethylate, thereafter the ethanol was distilled off until a precipitate formed. 3 ml of isopropyl ether were added to complete the precipitation. There were obtained 775 mg of p-t-butyl-N-[6-(2-hydroxyethoxy)-5-(o-methoxyphenoxy)-4-pyrimidinyl]benzenesulfonamide sodium, m.p.>250° C.

The starting material was prepared as follows:

c) 25 g of guaiacol and 37 g of dimethyl chloromalonate were added dropwise in succession to a sodium methylate solution from 150 ml of methanol and 4.6 g of sodium. The suspension was stirred at 45° C. for 1 hour with the exclusion of moisture, thereafter the methanol was distilled off. The residue was taken up in 200 ml of toluene and washed with water, 1% sodium hydroxide solution and water until the organic phase was colorless. After drying and evaporating the solvent, the residue was distilled. There were obtained 39.5 g of dimethyl (o-methoxyphenoxy)malonate. B.p. 128° C./7 Pa.

d) 5.5 g of formamidine acetate and 12.7 g of dimethyl (o-methoxyphenoxy)malonate were added while cooling with ice to a sodium methylate solution from 150 ml of methanol and 3.5 g of sodium. The reaction mixture was stirred at 0°–5° C. for 1 hour with the exclusion of moisture, then at room temperature for 2 hours. Thereafter, the solvent was distilled off, the residue was taken up in 100 ml of water, the aqueous phase was extracted with toluene and the organic phases were discarded. The aqueous phase was acidified, whereby 5-(o- methoxyphenoxy)-6-hydroxy-4(3H)-pyrimidinone separated.

e) 9.4 g of the previously obtained pyrimidinone were suspended in 20 ml of acetonitrile and treated with 12 g of collidine. Thereafter, 5 ml of POCl$_3$ in 15 ml of acetonitrile were added dropwise with the exclusion of moisture. The reaction mixture was stirred at reflux temperature for 8 hours, thereafter the solvent and excess reagent were distilled off. The residue was taken up in methylene chloride and washed with water, saturated sodium hydrogen carbonate solution and saturated sodium chloride solution. The solution was concentrated and passed over a short silica gel column with methylene chloride as the elution agent. The eluate was concentrated, the residue was recrystallized from ethanol/hexane. There were obtained 8.5 g of 4,6-dichloro-5-(o-methoxyphenoxy)pyrimidine, m.p. 79°-80° C.

f) 0.8 g of 4,6-dichloro-5-(o-methoxyphenoxy)pyrimidine and 1.5 g of p-t-butylsulfonamide K in 3 ml of dry dimethyl sulfoxide were heated to 120° C. under argon for 1.5 hours. Thereafter, the dimethyl sulfoxide was distilled off, the residue was partitioned between ethyl acetate and 1N hydrochloric acid and the organic phase was washed neutral. The organic phase was dried, the solvent was evaporated and the residue was treated with 3 ml of methanol. There were obtained 950 mg of p-t-butyl-N-[6-chloro-5-(o-methoxyphenoxy)-4-pyrimidinyl]benzenesulfonamide, m.p. 152° C.

EXAMPLE 2

In analogy to Example 1, paragraph a), from p-isopropyl-N-[6-chloro-5-(o-methoxyphenoxy)-4-pyrimidinyl]benzenesulphonamide there was obtained N-[6-(hydroxyethoxy)-5-(o-methoxyphenoxy)-4-pyrimidinyl]-p-isopropylbenzenesulfonamide, m.p. 142°-143° C. The compound was converted in analogy to Example 1, paragraph b), in almost quantitative yield into the water-soluble sodium salt.

The starting material was obtained in analogy to Example 1, paragraph f), by reacting 540 mg of 4,6-dichloro-5-(o-methoxyphenoxy)pyrimidine and 360 mg of p-isopropylbenzenesulfonamide potassium.

EXAMPLE 3

In analogy to Example 1, paragraph a), from N-[6-chloro-5-(o-tolyloxy)-4-pyrimidinyl]-p-t-butylsulfonamide there was obtained p-t-butyl-N-[6-(2-hydroxyethoxy)-5-(o-tolyloxy)-4-pyrimidinyl]benzenesulfonamide. M.p. 190°-192° C.

The starting material was prepared as follows:
Diethyl bromomalonate was converted with sodium o-cresolate into diethyl (o-tolyloxy)malonate, b.p. 120° C./7 Pa, in analogy to Example 1, paragraph c).

In analogy to Example 1, paragraph d), from the foregoing malonic ester there was obtained 5-(o-tolyloxy)-6-hydroxy-4(3H)-pyrimidinone from which there was obtained in analogy to Example 1e) 4,6-dichloro-(o-tolyloxy)pyrimidine, m.p. 78°-79° C. (ethanol/hexane). Reaction of the latter compound with p-t-butylsulfonamide potassium finally yielded N-[6-chloro-5-(o-tolyloxy)-4-pyrimidinyl]-p-t-butylsulfonamide.

EXAMPLE 4

In analogy to Example 1, paragraph a), from p-t-butyl-N-[2-chloro-5-(o,-chlorophenoxy)-4-pyrimidinyl]benzenesulphonamide there was obtained p-t-butyl-N-[6-(2-hydroxyethoxy)-5-(o-chloro-phenyloxy)-4-pyrimidinyl]benzenesulfonamide, m.p. 178°-179° C. (from diisopropyl ether).

The starting material was prepared as follows:
In analogy to Example 1, paragraph e), from diethyl bromomalonate and sodium o-chlorophenolate there was obtained diethyl (o-chlorophenoxy)malonate as a colorless liquid which was converted in analogy to Example 1, paragraph d), into 5-(o-chlorophenoxy)-6-hydroxy-4(3H)pyrimidinone. From the latter compound, there was obtained in analogy to Example 1, paragraph e), 4,6-dichloro-5-(o-chlorophenoxy)pyrimidine, m.p. 76°-77° C. (from ethanol/hexane), and from this by reaction with p-t-butylsulfonamide potassium there was obtained p-t-butyl-N-[2-chloro-5-(o-chlorophenoxy)-4-pyrimidinyl]benzenesulphonamide, m.p. 186°-187° C. (from methanol).

EXAMPLE 5

In an analogy to Example 1, paragraph a), from N-[6-chloro-5-(o-chlorophenoxy)-4-pyrimidinyl]-p-isopropylbenzenesulphonamide there was obtained N-[6-(2-hydroxyethoxy)-5-(o-chlorophenoxy)-4-pyrimidinyl]-p-isopropylbenzenesulfonamide, m.p. 174°-175° C. (from ethyl acetate).

The starting material was prepared in analogy to Example 1, paragraph f), from 4,6-dichloro-5-(o-chlorophenoxy)pyrimidine and p-isopropylbenzenesulfonamide potassium. M.p. 174°-176° C. (from methanol).

EXAMPLE 6

In analogy to Example 1, paragraph a), from p-t-butyl-N-[6-chloro-5-(m-methoxyphenoxy)-4-pyrimidinyl]benzenesulfonamide there was obtained p-t-butyl-N-[6-(2-hydroxyethoxy)-5-(m-methoxyphenoxy)-4-pyrimidinyl]benzenesulphonamide, m.p. 165°-167° C. (from diisopropyl ether).

The potassium salt, m.p. 213°-215° C., was obtained by reacting the sulfonamide with 0.5N KOH in ethanol.

The sodium salt was prepared in analogy to Example 1, paragraph b). M.p. 265°-270° C. (from diisopropyl ether).

The starting material was prepared as follows:
Diethyl bromomalonate was converted with sodium m-methoxyphenolate in analogy to Example 1, paragraph c), into diethyl (m-methoxyphenoxy)malonate, colorless liquid. B.p. 143° C./0.05 Torr. The thus-obtained malonic ester was converted in analogy to Example 1, paragraph d), into 5-(m-methoxyphenoxy)-6-hydroxy-4(3H)-pyrimidinone from which in analogy to Example 1, paragraph e), there was prepared 4,6-dichloro-5-(m-methoxyphenoxy)pyrimidine, m.p. 109°-110° C. Reaction of the last-named compound with p-t-butylbenzenesulfonamide potassium yielded p-t-butyl-N-[6-chloro-5-(m-methoxyphenoxy)-4-pyrimidinyl]benzenesulfonamide, m.p. 152° C. (from methanol).

EXAMPLE 7

In analogy to Example 1, paragraph a), from p-t-butyl-N-[6-chloro-5-phenoxy-4-pyrimidinyl]benzenesulfonamide there was obtained p-t-butyl-N-[6-(2-hydroxyethoxy)-5-phenoxy-4-pyrimidinyl]benzenesulfonamide, m.p. 165°-167° C. (from diisopropyl ether).

The starting material was prepared as follows:
Diethyl bromomalonate was converted with sodium phenolate in analogy to Example 1, paragraph c), into diethyl phenoxymalonate, b.p. 140° C./0.05 Torr. From the malonic ester, there was obtained in analogy to Example 1, paragraph e), 5-phenoxy-6-hydroxy-4(3H)pyrimidinone and from this there was obtained in analogy to Example 1, paragraph e), 4,6-dichloro-5-phenoxypyrimidine, m.p. 89°–90° C. (from ethanol/hexane). Reaction of the last-named compound with p-t-butylbenzenesulfonamide potassium yielded p-t-butyl-N-[6-chloro-5-phenoxy-4-pyrimidinyl]benzenesulfonamide, m.p. 143°–144° C.

EXAMPLE 8

In analogy to Example 1, paragraph a), from 4,6-dichloro-5-(p-methoxyphenoxy)-4-pyrimidine there was obtained p-t-butyl-N-[6-(2-hydroxyethoxy)-5-(p-methoxyphenoxy)-4-pyrimidinyl]benzenesulfonamide, m.p. 141°–142° C.

The starting material was prepared in analogy to Example 1, paragraph c), d) and e), by reacting diethyl bromomalonate with sodium p-methoxyphenolate to diethyl (p-methoxyphenoxy)malonate, b.p. 140° C./7 Pa, and reaction further to 5-(p-methoxyphenoxy)-6-hydroxy-4(3H)pyrimidinone and, respectively, 4,6-dichloro-5-(p-methoxyphenoxy)-4-pyrimidine, m.p. 107°–108° C. (from ethanol/hexane).

EXAMPLE 9

In analogy to Example 1, paragraph a), from p-t-butyl-N-[6-chloro-5-(o-ethoxyphenoxy)-4-pyrimidinyl]-benzenesulfonamide there was obtained p-t-butyl-N-[6-(2-hydroxyethoxy)-5-(o-ethoxyphenoxy)-4-pyrimidinyl]benzenesulfonamide, m.p. 120°–121° C. (from diisopropyl ether).

The starting material was prepared from dimethyl chloromalonate in analogy to Example 1, paragraph c), d), e) and f), via the following intermediates:

Dimethyl (o-ethoxyphenoxy)malonate, b.pt. 150° C./7 Pa,
5-(o-ethoxyphenoxy)-6-hydroxy-4(3H)pyrimidinone,
4,6-dichloro-5-(o-ethoxyphenoxy)-4-pyrimidine,
5-p-t-butyl-N-[6-chloro-5-(o-ethoxyphenoxy)-4-pyrimidinyl]benzenesulfonamide, m.p. 162°–163° C. (from methanol).

EXAMPLE 10

In analogy to Example 1, paragraph a), from p-(2,2-dimethylpropyl)-N-[6-chloro-5-(o-methoxyphenoxy)-4-pyrimidinyl]benzenesulfonamide there was obtained p-(2,2-dimethylpropyl)-N-[6-(2-hydroxyethoxy)-5-(o-methoxyphenoxy)-4-pyrimidinyl]benzenesulfonamide, m.p. 136°–137° C. (from diisopropyl ether).

The starting material was prepared in analogy to Example 1, paragraph c), d) and f), via the following intermediates:

p-(2,2-Dimethylpropyl)benzenesulphonyl chloride, b.p. 105° C./0.005 Torr.,
2,2-dimethyl-p-(2,2-dimethylpropyl)benzenesulfonamide potassium,
p-(2,2-dimethylpropyl)-N-[6-chloro-5-(o-methoxyphenoxy)-4-pyrimidinyl]benzenesulfonamide, m.p. 164°–165° C. (from methanol).

EXAMPLE 11

In analogy to Example 1, paragraph a), from N-[6-chloro-2-methyl-5-(m-methoxyphenoxy)-4-pyrimidinyl]-p-isopropylbenzenesulfonamide, m.p. 152°–153° C., there was obtained p-iso-propyl-N-[6-(2-hydroxyethoxy)-2-methyl-5-(m-methoxyphenoxy)-4-pyrimidinyl]benzenesulfonamide, m.p. 129°–130° C. (from diisopropyl ether).

The starting material was prepared as follows:

In analogy to Example 1, paragraph e), using acetamidine hydrochloride in place of formamidine acetate, dimethyl (m-methoxyphenoxy)malonate was converted into 5-(m-methoxyphenoxy)-2-methyl-6-hydroxy-4(3H)pyrimidinone. Therefrom, there was prepared in analogy to Example 1, paragraph e), 4,6-dichloro-2-methyl-5-(m-methoxyphenoxy)pyrimidine and therefrom with p-isopropylbenzenesulfonamide potassium there was prepared N-[6-chloro-2-methyl-5-(m-methoxyphenoxy)-4-pyrimidinyl]-p-isopropylbenzenesulfonamide, m.p. 152°–153° C. (from methanol).

EXAMPLE 12

In analogy to Example 1, paragraph a), from N-[6-chloro-5-(-(o-methoxy)-2-phenyl-4-pyrimidinyl]-p-isopropylbenzenesulfonamide there was obtained N-[6-(2-hydroxyethoxy)-5-(o-methoxyphenoxy)-2-phenyl-4-pyrimidinyl]-p-isopropylbenzenesulfonamide.

The starting material was prepared in analogy to Example 1, paragraph d), e) and f), from dimethyl (o-methoxyphenoxy)malonate via 5-(o-methoxy)-2-phenyl-6-hydroxy-4(3H)-pyrimidinone, 4,6-dichloro-2-phenyl-5-(o-methoxyphenoxy)pyrimidine, m.p. 135°–136° C., and N-[6-chloro-5-(o-methoxy)-2-phenyl-4-pyrimidinyl]-p-isopropylbenzenesulfonamide, m.p. 190°–191° C. (from methanol).

EXAMPLE 13

1.3 ml of 1.6M butyllithium in hexane were added at −20° C. to 780 mg of benzyltriphenylphosphonium chloride in 10 ml of abs. tetrahydrofuran. The reaction mixture was stirred at −20° C. for 15 minutes and thereafter treated with 280 mg of 2-[(5-formyl-6-p-toluenesulphonamido-4-pyrimidinyl)oxy]ethyl acetate. The reaction mixture was left to warm to room temperature and was stirred at room temperature for 2 hours. The tetrahydrofuran was distilled off under reduced pressure, the residue was dissolved in ethyl acetate and the organic phase was washed with water and saturated sodium chloride solution, dried and evaporated. The residue was chromatographed over silica gel with methylene chloride/ethyl acetate (9:1 and 8:2). There were obtained 160 mg of 2-[[5-[(E/Z)-styryl]-6-p-toluenesulphonamido-4-pyrimidinyl]oxy]ethyl acetate, m.p. 146°–156° C.

The starting material was prepared as follows:

From 5-allyl-4,6-dichloropyrimidine-p-toluenesulfonamide potassium there was prepared N-[6-chloro-5-[(E/Z)-propenyl]-4-pyrimidinyl]-p-toluenesulfonamide and therefrom by reaction with ethylene glycol sodium there was prepared N-[6-(2-hydroxyethoxy)-5-[(E/Z)-propenyl]-4-pyrimidinyl]-p-toluenesulphonamide, m.p. 130°–132° C. Reaction with acetic anhydride in the presence of pyridine in tetrahydrofuran yielded 2-[[5-[(E/Z)-propenyl]-6-p-toluenesulphonamido-4-pyrimidinyl]oxy]ethyl acetate, m.p. 160°–163° C.

390 mg of the previously named compound and 8 mg of osmium tetroxide were added to a mixture of 2.5 ml of water and 7 ml of dioxan and then 450 mg of sodium m-periodate were added at room temperature within 30 minutes and after stirring at room temperature for 2 hours a further 8 mg of osmium tetroxide were added. The reaction mixture was stirred for a further 5 hours and worked-up, whereby 2-[(5-formyl-6-p-toluenesulphonamido-4-pyrimidinyl)oxy]ethyl acetate, m.p. 130°–144° C. (after crystallization from ethyl acetate and diethyl ether), was obtained.

EXAMPLE 14

120 mg of 2-[[5-[(E/Z)-styryl]-6-p-toluenesulphonamido-4-pyrimidinyl]oxy]ethyl acetate were hydrogenated in 3 ml of abs. ethanol and 3 ml of abs. tetrahydrofuran in the presence of 4 mg of 5% palladium/charcoal. After completion of the hydrogen uptake, the catalyst was filtered off and the organic phases were evaporated under reduced pressure. The residue was chromatographed on silica gel with ethyl acetate and yielded 110 mg of 2-[[5-phenethyl-6-p-toluenesulphonamido-4-pyrimidinyl]oxy]ethyl acetate, m.p. 120°–123° C.

EXAMPLE 15

80 mg of 2-[(5-phenethyl-6-p-toluenesulphonamido-4-pyrimidinyl)oxy]ethyl acetate in 5 ml of methanol were stirred with 53 mg of finely powdered potassium carbonate at 20° C. for 15 hours. Thereafter, the methanol was removed under reduced pressure, the residue was taken up in ethyl acetate, the organic phase was washed with water and saturated sodium chloride solution, dried and evaporated. The residue was chromatographed over silica gel with methylene chloride/ethyl acetate(1:1) and ethyl acetate. There were obtained 40 mg of N-[6-(2-hydroxyethoxy)-5-phenethyl-4-pyrimidinyl]-p-toluenesulfonamide as a white resin.

EXAMPLE 16

In analogy to Example 15, from 2-[[5-[(E/Z)-styryl]-6-p-toluenesulphonamido]-4-pyrimidinyl]oxy]ethyl acetate there was obtained N-[6-(2-hydroxyethoxy)-5-[(E/Z)-styryl]-4-pyrimidinyl]-p-toluenesulfonamide as a white resin.

EXAMPLE 17

In analogy to Example 1, paragraph a), from N-[6-chloro-5-(2,4,6-trichlorophenoxy)-4-pyrimidinyl]-p-isopropylbenzenesulfonamide and ethylene glycol Na there was obtained N-[6-(2-hydroxyethoxy)-5-(2,4,6-trichlorophenoxy)-4-pyrimidinyl]-p-isopropylbenzenesulfonamide, m.p. 182°–183° C. (from methylene chloride and isopropyl ether).

The starting material was prepared from 4,6-dichloro-5-(2,4,6-trichlorophenoxy)pyrimidine and p-isopropylbenzenesulfonamide, m.p. 217°–218° C. (from methylene chloride and isopropyl ether).

EXAMPLE 18

In analogy to Example 1, paragraph a), from N-[6-chloro-5-(2,4,6-trichlorophenoxy)-4-pyrimidinyl]-o-toluenesulfonamide and ethylene glycol Na there was obtained N-[6-(2-hydroxyethoxy)-6-(2,4,6-trichlorophenoxy)-4-pyrimidinyl]-o-toluenesulfonamide, m.p. 144°–145° C. (from isopropyl ether).

The starting material was prepared from 4,6-dichloro-5-(2,4,6-trichlorophenoxy)-pyrimidine and o-toluenesulfonamide, m.p. 107°–109° C. (from isopropyl ether).

EXAMPLE 19

In analogy to Example 1, paragraph a), from N-[6-chloro-5-(2,4,6-trichlorophenoxy)-4-pyrimidinyl]-2,4-xylenesulfonamide and ethylene glycol Na there was obtained N-[6-(2-hydroxyethoxy)-5-(2,4,6-trichlorophenoxy)-4-pyrimidinyl]-2,4-xylenesulfonamide, m.p. 157°–158° C. (from isopropyl ether).

The starting material was prepared as follows:

16.9 g of anhydrous $K_2CO_3$ were added to a solution of 18.0 g of 2,4,6-trichlorophenol and 32.0 g of diethyl bromomalonate in 180 ml of acetone and 20 ml of toluene. The reaction mixture was heated at reflux while stirring for 24 hours, the solution was filtered off from the precipitate and evaporated under reduced pressure. The residue was taken up in toluene, the organic solution was washed with a 5% sodium carbonate solution, then with water, dried over sodium sulphate and, after filtering off the salt under suction, evaporated under reduced pressure. The residue was distilled under $\leq 1$ mmHg pressure, whereby there was obtained a colourless oil (b.p. 171°–174° C.) from which with formamidine acetate and sodium methylate there was obtained 5-(2,4,6-trichlorophenoxy)-4,6(3H, 5H)-pyrimidinedione, m.p. >270° C., which, prior to the further reaction, was dried at 80° C. overnight under reduced pressure.

A solution of 7.6 g of 5-(2,4,6-trichlorophenoxy)-4,6-(3H,5H)-pyrimidinedione, 6.6 g of tetraethylammonium chloride, 3.3 ml of collidine, 13.7 ml of $POCl_3$ in 70 ml of $CH_3CN$ was heated at reflux for 4.5 hours, the solution was evaporated under reduced pressure, the residue was treated three times with ether, the combined organic solutions were filtered overnight, evaporated under reduced pressure and the residue was recrystallized from ether and n-hexane. There was obtained 4,6-dichloro-5-(2,4,6-trichlorophenoxy)pyrimidine, m.p. 104°–105° C.

From 4,6-dichloro-5-(2,4,6-trichlorophenoxy)pyrimidine and 2,4-xylenesulfonamide there was obtained N-[6-chloro-5-(2,4,6-trichlorophenoxy)-4-pyrimidinyl]-2,4-xylenesulphonamide, m.p. 267° C. (from acetonitrile and isopropyl ether).

EXAMPLE 20

By reacting 4,6-dichloro-5-[(2-methoxy-4-methyl)-phenoxy]pyrimidine with p-t-butylbenzenesulfonamide and thereafter with ethylene glycol Na there was obtained p-t-butyl-N-[6-(2-hydroxyethoxy)-5-[(2-methoxy-p-tolyl)oxy]-4-pyrimidinyl]benzenesulfonamide as a solid.

The starting material was prepared by the reaction of methylguaiacol with diethyl bomomalonate and thereafter with formamidine acetate to give 5-[(2-methoxy-4-methyl)phenoxy]-4,6(3H, 4H)-pyrimidinedione, m.p. 234°–236° C., and further reaction of the latter compound with $POCl_3$.

EXAMPLE 21

By reacting 4,6-dichloro-5-[(2-methoxy-4-methyl)-phenoxy]pyrimidine with p-isopropylbenzenesulfonamide and thereafter with ethylene glycol Na there was obtained N-[5-(2-methoxy-4-methyl)phenoxy]-6-(2-hydroxyethoxy)-4-pyrimidinyl]-p-isopropylbenzenesulfonamide, m.p. 135°–136° C. (from ethyl acetate).

EXAMPLE 22

By reacting 4,6-dichloro-5-[(2-methoxy-4-methyl)-phenoxy]pyrimidine with o-ethylbenzenesulfonamide and thereafter with ethylene glycol Na there was obtained N-[5-(2-methoxy-4-methyl)phenoxy-6-(2-hydroxyethoxy)-4-pyrimidinyl]-o-ethylbenzenesulfonamide as a solid.

EXAMPLE 23

By reacting 4,6-dichloro-5-(2-methoxy)phenoxy-2-methylpyrimidine with p-tert-butylphenylsulfonamide and thereafter with ethylene glycol Na there was obtained p-tert-butyl-N-[6-(2-hydroxyethoxy)-5-(o-methoxyphenoxy)-2-methyl-4-pyrimidinyl]benzenesulfonamide, m.p. 123°-124° C. (from ethyl acetate).

EXAMPLE 24

By reacting 4,6-dichloro-5-(2-methoxy)phenoxy-2-methylpyrimidine with p-isopropylbenzenesulfonamide and thereafter with ethylene glycol Na there was obtained N-[6-(2-hydroxyethoxy)-5-(o-methoxyphenoxy)-2-methyl-4-pyrimidinyl]-p-isopropylbenzenesulfonamide, m.p. 124°-126° C. (from acetonitrile, isopropanol and water).

EXAMPLE 25

By reacting 4,6-dichloro-5-(2-methoxyphenoxy)-2-trifluoromethylpyrimidine with p-isopropylbenzenesulfonamide and thereafter with ethylene glycol Na there was obtained N-[6-(2-hydroxyethoxy)-5-(o-methoxyphenoxy)-2-trifluoromethyl)-4-pyrimidinyl]-p-isopropylbenzenesulfonamide as a solid.

EXAMPLE 26

By reacting 4,6-dichloro-5-(2-methoxyphenoxy)-2-trifluoromethylpyrimidine with p-tert-butylbenzenesulfonamide and with ethylene glycol Na there was obtained p-tert-butyl-N-[6-(2-hydroxyethoxy)-5(o-methoxyphenoxy)-2-(trifluoromethyl)-4-pyrimidinyl]-benzenesulfonamide, m.p. 190°-192° C. (from toluene). Sodium salt: M.p. 288°-289° C.

EXAMPLE 27

By reacting 5-(1,3-benzodioxol-5-yloxy)-4,6-dichloropyrimidine with p-tert-butylphenylsulfonamide and thereafter with ethylene glycol Na, there was obtained N-[5-(1,3-benzodioxol-5-yloxy)-6-(2-hydroxyethoxy)-4-pyrimidinyl]-p-tert-butylbenzenesulfonamide as a solid.

EXAMPLE 28

By reacting 5-(1,3-benzodioxol-5-yloxy)-4,6-dichloropyrimidine with p-isopropylbenzenesulfonamide and thereafter with ethylene glycol Na, there was obtained N-[5-(1,3-benzodioxol-5-yloxy)-6-(2-hydroxyethoxy)-4-pyrimidinyl]-p-isopropylbenzenesulfonamide as a solid.

EXAMPLE 29

By reacting 5-(2-methoxyphenoxy)-4,6-dichloropyrimidine with o-methoxyphenylsulfonamide and thereafter with ethylene glycol Na, there was obtained N-[6-(2-hydroxyethoxy)-5-(o-methoxyphenoxy)-4-pyrimidinyl]-o-methoxybenzenesulfonamide, m.p. 164°-165° C. (from ethyl acetate).

EXAMPLE 30

By reacting p-tert-butyl-N-[6-chloro-5-(o-methoxyphenoxy)-2-methyl-4-pyrimidinyl]benzenesulfonamide with the monosodium salt of 1,4-butanediol, there was obtained p-tert-butyl-N-[6-(4-hydroxybutoxy)-5-(o-methoxyphenoxy)-2-methyl-4-pyrimidinyl]benzenesulfonamide as a white foam.

EXAMPLE 31

By reacting 4,6-dichloro-5-(2-naphthyloxy)pyrimidine with p-isopropylphenylsulfonamide and thereafter with the sodium salt of ethylene glycol, there was obtained N-[6-(2-hydroxyethoxy)-5-(2-naphthyloxy)-4-pyrimidinyl]-p-isopropylbenzenesulfonamide, m.p. 160°-161° C. (from isopropyl ether).

EXAMPLE 32

By reacting 4,6-dichloro-5-(2-naphthyloxy)pyrimidine with p-tert-butylphenylsulfonamide and thereafter with ethylene glycol Na, there was obtained N-[6-(2-hydroxyethoxy)-5-(2-naphthyloxy)-4-pyrimidinyl]-p-tert-butylbenzenesulfonamide, m.p. 197°-198° C. (from isopropyl ether).

EXAMPLE 33

By reacting 4,6-dichloro-5-(o-methoxyphenoxy)-2-propylpyrimidine with p-isopropylphenylsulfonamide and thereafter with ethylene glycol Na, there was obtained N-[6-(2-hydroxyethoxy)-5-(o-methoxyphenoxy)-2-propyl-4-pyrimidinyl]-p-isopropylbenzenesulfonamide as a solid.

EXAMPLE 34

By reacting 4,6-dichloro-5-(o-methoxyphenoxy)-2-propylpyrimidine with p-tert-butylphenylsulfonamide and thereafter with ethylene glycol Na, there was obtained p-tert-butyl-N-[6-(2-hydroxyethoxy)-5-(o-methoxyphenoxy)-2-propyl-4-pyrimidinyl]-benzenesulfonamide.

EXAMPLE 35

By reacting 4,6-dichloro-5-(o-methoxy)phenoxy-2-methylpyrimidine with α,α,α-trifluoro-p-toluenesulfonamide and thereafter with ethylene glycol Na, there was obtained α,α,α-trifluoro-N-[6-(2-hydroxyethoxy)-5-(o-methoxyphenoxy)-2-methyl-4-pyrimidinyl]-p-toluenesulfonamide, m.p. 144°-145° C. (from ethyl acetate).

EXAMPLE 36

By reacting 4,6-dichloro-5-(o-methoxy)phenoxy-2-methylpyrimidine with p-chlorophenylsulfonamide and thereafter with ethylene glycol Na, there was obtained p-chloro-N-[6-(2-hydroxyethoxy)-5-(o-methoxyphenoxy)-2-methyl-4-pyrimidinyl]benzenesulfonamide, m.p. 134°-135° C. (from ethyl acetate).

EXAMPLE 37

By reacting 4,6-dichloro-5-(o-methoxy)phenoxy-2-methylpyrimidine with p-(trifluoromethoxy)benzenesulfonamide and thereafter with ethylene glycol Na, there was obtained N-[6-(2-hydroxyethoxy)-5-(o-methoxyphenoxy)-2-methyl-4-pyrimidinyl]-p-(trifluoromethoxy)benzenesulfonamide, m.p. 138°-140° C. (from ethyl acetate).

EXAMPLE 38

By reacting 4,6-dichloro-5-(o-methoxyphenoxy)-2-methylpyrimidine with o-ethylbenzenesulfonamide and thereafter with ethylene glycol Na, there was obtained o-ethyl-N-[6-(2-hydroxyethoxy)-5-(o-methoxyphenoxy)-2-methyl-4-pyrimidinyl]benzenesulfonamide as a white foam.

EXAMPLE 39

By reacting 4,6-dichloro-5-(o-methoxy)phenoxy-2-methylpyrimidine with p-toluenesulfonamide thereafter with ethylene glycol Na, there was obtained N-[6-(2-hydroxyethoxy)-5-(o-methoxyphenoxy)-2-methyl-4-pyrimidinyl]-p-toluenesulfonamide as a white foam.

EXAMPLE 40

By reacting 4,6-dichloro-5-(o-methoxy)phenoxy-2-methylpyrimidine with 2-naphthylsulfonamide and thereafter with ethylene glycol Na, there was obtained N-[6-(2-hydroxyethoxy)-5-(o-methoxyphenoxy)-2-methyl-4-pyrimidinyl]-2-naphthylsulfonamide as a foam.

EXAMPLE 41

By reacting p-tert-butyl-N-[6-chloro-5-(o-methoxyphenoxy)-2-methyl-4-pyrimidinyl]benzenesulfonamide with the monosodium salt of 1,3-propanediol, there was obtained p-tert-butyl-N-[6-(3-hydroxypropoxy)-5-(o-methoxyphenoxy)-2-methyl-4-pyrimidinyl]benzenesulfonamide as a white foam.

EXAMPLE 42

In analogy to Example 1, paragraph a), 300 mg of p-t-butyl-N-[6-chloro-5-[(o-methylthio)phenoxy]-4-pyrimidinyl]benzenesulfonamide were converted into N-[6-(2-hydroxyethoxy)-5-[(o-methylthio)phenoxy]-4-pyrimidinyl]benzenesulfonamide. There were obtained 250 mg of p-t-butyl-N-[6-(2-hydroxyethoxy)-5-[(o-methylthio)phenoxy]-4-pyrimidinyl]benzenesulfonamide, m.p. 149°-150° C.

The starting material was prepared as follows:

a) Dimethyl (o-methylthio)phenoxymalonate was obtained from dimethyl chloromalonate and (o-methylthio)phenol in analogy to Example 1, paragraph c). From 17 g of (o-methylthio)phenol there were obtained 23 g of malonate from toluene-hexane.

b) 9.15 g of 5-[(o-methylthio)phenoxy]-6-hydroxy-4-(3H)-pyrimidinone, MS:250 (M), were obtained from 13.5 g of the malonate from a) and formamidine acetate in analogy to Example 1, paragraph d).

c) 2.5 g of this compound and 2.9 g of diisopropylethylamine were suspended in 15 ml of acetonitrile. 2 ml of POCl$_3$ were added dropwise to the suspension and the mixture was subsequently boiled at reflux for 5 hours. 4,6-Dichloro-5-[(o-methylthio)phenoxy]pyrimidine was obtained after working-up in analogy to Example 1, paragraph e). After crystallization from n-hexane, there was obtained 1 g of pyrimidine derivative, m.p. 89°-90° C.

d) In analogy to Example 1, paragraph f), 580 mg of 4,6-dichloro-5-[(o-methylthio)phenoxy]pyrimidine were converted with 850 mg of p-t-butylbenzenesulfonamide K into p-t-butyl-N-[6-chloro-5-[(o-methylthio)phenoxy]-4-pyrimidinyl]benzenesulfonamide. After crystallization from MeOH, there were obtained 480 mg of white crystals, m.p. 154°-155° C.

EXAMPLE 43 a) In analogy to Example 1, paragraph a), 350 mg of p-t-butyl-N-[(6-chloro-5-(o-methoxyphenoxy)-2-phenyl-4-pyrimidinyl]benzenesulfonamide were converted into p-t-butyl-N-[6-(2-hydroxyethoxy)-5-(o-methoxyphenoxy)-2-phenyl-4-pyrimidinyl]benzenesulfonamide. After crystallization from diisopropyl ether, there were obtained 330 mg of white crystals, m.p. 160°-161° C.

b) 225 mg of this compound were dissolved in EtOH. The stoichiometric amount of KOH in MeOH was added to the solution. Then, the solvent was distilled off and diisopropyl ether was added to the residue, whereby there was obtained p-t-butyl-N-[6-(2-hydroxyethoxy)-5-(o-methoxyphenoxy)-2-phenyl-4-pyrimidinyl]benzenesulfonamide potassium, MS: 588 [(M+K)+].

EXAMPLE 44

In analogy to Example 1, paragraph a), from N-[2-amino-6-chloro-5-(o-methoxyphenoxy)-4-pyrimidinyl]-p-tert.-butylbenzenesulfonamide, there was obtained N-[2-amino-6-(2-hydroxyethoxy)-5-(o-methoxyphenoxy)-4-pyrimidinyl]-p-tert.-butylbenzenesulfonamide, white crystals of melting point 168° C. (from diisopropyl ether).

The starting material was prepared as follows:

a) 7.65 g of dimethyl (5-o-methoxy)phenoxymalonate and 3 g of guanidine hydrochloride were added to a solution of 2.3 g of Na in 100 ml of methanol. The suspension was stirred at room temperature under argon for 3 hours. Then, the methanol was distilled off and the residue was taken up in H$_2$O. After the usual treatment, as already described, the compound was precipitated by the dropwise addition of acetic acid until the pH of the solution had reached 4.5. There were obtained 6.4 g of crude product of which 1.35 g were suspended in 10 ml of dioxan. 1.4 g of N-ethyldiisopropylamine, 2 ml of POCl$_3$ and 1 g of triethylbenzylammonium chloride were added thereto in succession. The mixture was boiled at reflux under an argon atmosphere while stirring vigorously. After 30 minutes, the solvent mixture was distilled off, the residue was taken up in ethyl acetate and extracted with H$_2$O and saturated NaHCO$_3$ solution. Purification was carried out by chromatography on silica gel (CH$_2$Cl$_2$-ethyl acetate, 9:1 vol., as the eluent). There was obtained 2-amino-4,6-dichloro-5-(o-methoxyphenoxy)pyrimidine as a colorless solid. M.p. 190° C.

b) 0.5 g of the foregoing dichloro compound and 0.75 g of p-tert.-butylbenzenesulfonamide Na in 2 ml of DMSO were converted at 90° C. into N-[2-amino-6-chloro-5-(o-methoxyphenoxy)-4-pyrimidinyl]-p-tert-butylbenzenesulfonamide, m.p. 194°-195° C.

EXAMPLE 45 a) In analogy to Example 1, paragraph a), 478 mg of p-tert-butyl-N-[6-chloro-2-methyl-5-[o-(methylthio)phenoxy]pyrimidinyl]benzenesulfonamide and Na glycolate in ethylene glycol were converted into p-tert-butyl-N-[6-(2-hydroxyethoxy)-2-methyl-5-[o-(methylthio)phenoxy]-4-pyrimidinyl]benzenesulfonamide, m.p. 166°-167° C.

b) 225 mg of this compound were converted into the sulphonamide salt by adding the stoichiometric amount of aqueous NaOH. Then, it was diluted with methanol to give a homogeneous solution. 100 mg of NaIO$_4$ dissolved in 2 ml of H$_2$O were added to this solution and the mixture was stirred at room temperature for 8 hours. Then, it was evaporated to dryness. The residue was partitioned between ethyl acetate and aqueous 0.1N H$_2$SO$_4$. After evaporating the organic phase, the p-tert-butyl-N-[6-(2-hydroxyethoxy)-2-methyl-5-[o-(R,S-methylsulphinyl)phenoxy]-4-pyrimidinyl]benzenesulfonamide was crystallized from diisopropyl ether. 150 mg of white crystals were obtained. MS: m/e=520 (M+H)+.

The starting material was prepared as follows:

5.4 g of dimethyl (o-methylthiophenoxy)malonate and 2.1 g of acetamidine hydrochloride were converted into 6-hydroxy-2-methyl-5-[o-(methylthio)phenoxy]-4(3H)-pyrimidine and this was converted into 4,6- dichloro-2-methyl-5-[o-(methylthiophenoxy)]-pyrimidine, m.p. 132°–133° C.

0.9 g of the foregoing dichloro compound and 1.3 g of p-tert-butylbenzenesulfonamide K were converted into p-tert-butyl-N-[6-chloro-2-methyl-5-[o-methylthio)phenoxy]-4-pyrimidinyl]benzenesulfonamide. M.p. 162°–163° C.

EXAMPLE 46

1.22 g of (S)-1,2-di-O-isopropylidene-glycerol were added dropwise under an argon atmosphere to a suspension of 170 mg of NaH in 2 ml of dry THF. Subsequently, 1.03 g of p-tert-butyl-N-[6-chloro-5-(o-methoxyphenoxy)-2-(p-methoxyphenyl)-4-pyrimidinyl]benzenesulfonamide and 2 ml of DMSO were added. The mixture was left to react at 95° C. for 4 hours, whereby the THF distilled off. Then, 0.5 ml of $H_2O$ was added and the solvent mixture and the excess reagent were distilled off under reduced pressure. The residue was taken up in 20 ml of dioxan; 1 ml of aqueous 1N HCl was added and the mixture was left to react at 65° C. for 45 minutes. The mixture was then evaporated to dryness. The residue was partitioned between ethyl acetate and 1N hydrochloric acid. After the usual working-up, the compound was purified on silica gel with ethyl acetate as the eluent. There was obtained 0.98 g of (S)-4-tert-butyl-N-[6-(2,3-dihydroxypropyloxy)-5-(o-methoxy-phenoxy)-2-(p-methoxyphenyl)pyrimidin-4-yl]-benzenesulfonamide, m.p. 141°–142° C. (from diethyl ether).

The starting material was prepared as follows:

In analogy to Example 1, paragraph d), 7.63 g of dimethyl (o-methoxyphenoxy)malonate and 5.6 g of p-methoxy-benzamidine hydrochloride were condensed to give 2-(p-methoxyphenyl)-5-(o-methoxyphenoxy)-6-hydroxy-4(3H)-pyrimidinone. Reaction of this compound in analogy to Example 1, paragraph e), yielded 4,6-dichloro-2-(p-methoxyphenyl)-5-(o-methoxy-phenoxy)-pyrimidine, m.p. 113°–114° C., from which in analogy to Example 1, paragraph f), there was obtained p-tert-butyl-N-[6-chloro-5-(o-methoxyphenoxy)-2-(p-methoxyphenyl)-4-pyrimidinyl]benzenesulfonamide, m.p. 221°–222° C.

EXAMPLE 47

210 mg of 4-tert-butyl-N-[5-(2-chloro-5-methoxy-phenoxy)-2-ethyl-6-(2-methylsulphanyl-ethoxy)-pyrimidin-4-yl]-benzenesulfonamide were dissolved in 5 ml of MeOH and 0.2 ml of 1N NaOH. 95 mg of $NaIO_4$ dissolved in 0.5 ml of $H_2O$ were added thereto and the mixture was stirred at room temperature for 5 hours, whereby a suspension resulted. Then, 0.2 ml of 1N HCl was added and the mixture was subsequently evaporated to dryness. The residue was partitioned between ethyl acetate and 0.1N HCl and worked-up as usual. For purification, the compound was chromatographed on silica gel using ethyl acetate-MeOH (6:1 by vol.) as the eluent. There were obtained 160 mg of (RS)-4-tert-butyl-N-[5-(2-chloro-5-methoxy-phenoxy)-2-ethyl-6-(2-methylsulphinyl-ethoxy)pyrimidin-4-yl]-benzenesulfonamide as a white powder. MS: 581 (M).

The starting material was prepared as follows:

In analogy to Example 1, paragraph c), from 2-chloro-5-methoxy-phenol and dimethyl chloromalonate there was obtained dimethyl (2-chloro-5-methoxy-phenoxy)malonate, m.p. 68°–69° C. Condensation with propanidine hydrochloride yielded 2-ethyl-5-(2-chloro-5-methoxy-phenoxy)-6-hydroxy-4(3H)-pyrimidinone from which in analogy to Example 1, paragraph e), there was obtained 4,6-dichloro-2-ethyl-5-(2-chloro-5-methoxy-phenoxy)pyrimidine, m.p. 113°–113.5° C. This compound was converted analogously to Example 1, paragraph f), into 4-tert-butyl-N-[6-chloro-5-(2-chloro-5-methoxy-phenoxy)-2-ethyl-pyrimidin-4-yl]-benzenesulfonamide, m.p. 142°–143° C. (from ethanol).

300 mg of 2-(methylthio)ethanol were added dropwise under argon to a suspension of 63 mg of NaH in dry THF. Subsequently, 300 mg of the previously obtained sulfonamide and 1 ml of 1,3-dimethyl-3,4,5,6-tetrahydro-2(1H)-pyrimidinone were added thereto. The mixture was left to react at 80° C. for 3 hours. After the usual working-up of the reaction mixture and purification on silica gel ($CH_2Cl_2$-diethyl ether, 95/5 vol, as the eluent), there were obtained 160 mg of 4-tert-butyl-N-[5-(2-chloro-5-methoxy-phenoxy)-2-ethyl-6-(2-methyl-sulphanylethoxy)-pyrimidin-4-yl]-benzenesulfonamide as a white powder.

EXAMPLE 48 a) In analogy to Example 1, from 4-tert-butyl-N-[6-chloro-5-(2-chloro-5-methoxy-phenoxy)-2-methyl-pyrimidine-4-yl]-benzenesulfonamide there were manufactured 4-tert-butyl-N-[5-(2-chloro-5-methoxy-phenoxy)-6-(2-hydroxy-ethoxy)-2-methylpyrimidin-4-yl]-benzenesulfonamide. From 500 mg of the starting material, there were obtained 430 mg of white crystals. M.p. 141°–141.5° C. (from isopropyl ether).

b) 140 mg of the compound obtained were esterified with 3-furancarboxylic acid under the following conditions: 140 mg of the previously obtained sulfonamide, 170 mg of N-ethyl-N'-(3-dimethylaminopropyl)-carbodiimide hydrochloride, 170 mg of $Et_3N$ and 5 mg of dimethylamino pyridine were dissolved in 2 ml of dichloromethane and the solution was left to stand at room temperature for 24 hours. Then, 5 ml of THF and 1 ml of $H_2O$ were added thereto and the solution was stirred for 30 minutes. Subsequently, it was evaporated to dryness. The residue was partitioned between dichloromethane and 1N HCl, then washed three times with $H_2O$ and isolated as usual. The compound was purified on silica gel using dichloromethane-diethyl ether (95:5 by vol.) as the eluent. There were obtained 120 mg of 4-tert-butyl-N-[5-(2-chloro-5-(2-chloro-5-methoxy-phenoxy)-6-(2-(3-furoyloxy)ethoxy)-2-methyl-pyrimidin-4-yl]-benzenesulfonamide.

The starting material was prepared as follows:

In analogy to Example 1, paragraph d), dimethyl (2-chloro-5-methoxy-phenoxy)malonate was condensed with acetamidine hydrochloride to give (2-chloro-5-methoxy-phenoxy)-2-methyl-6-hydroxy-4(3H)-pyrimidinone. Therefrom in analogy to Example 1, paragraph e), there was obtained 4,6-dichloro-5-(2-chloro-5-methoxy-phenoxy)-2-methyl-pyrimidine, m.p. 125°–130° C., and therefrom in analogy to Example 1, paragraph f), there was obtained 4-tert-butyl-N-[6-chloro-5-(2-chloro-5-methoxyphenoxy)-2-methyl-pyrimidin-4-yl]-benzenesulfonamide, m.p. 182° C. (from MeOH).

EXAMPLE 49

In analogy to Example 47, 90 mg of N-[5-(2-chloro-5-methoxy-phenoxy)-6-(2-methylsulphanyl-ethoxy)-pyrimidin-4-yl]-1,3-benzodioxol-5-sulfonamide were oxidized with $NaIO_4$ to give (RS)-N-[5-(2-chloro-5-methoxy-phenoxy)-6-(2-methylsulphinyl-ethoxy)-pyrimidin-4-yl]-1,3-benzodioxol-5-sulphonamide. There were obtained 65 mg of white powder. MS: 542.1 (M+H+).

The starting material was prepared as follows:

In analogy to Example 1, paragraph d), dimethyl (2-chloro-5-methoxy-phenoxy)malonate was condensed with formamidine acetate to give (2-chloro-5-methoxy-phenoxy)-6-hydroxy-4(3H)-pyrimidinone. Therefrom in analogy to Example 1, paragraph e), there was obtained 4,6-dichloro-5-(2-chloro-2methoxyphenoxy)-pyrimidine, m.p. 88°–89° C. (from ethanol).

Reaction of 611 mg of 4,6-dichloro-5-(2-chloro-2-methoxy-phenoxy)-pyrimidine with 813 mg of 1,3-benzodioxol-5-sulfonamide K yielded 535 mg of N-[6-chloro-5-(2-chloro-5-methoxy-phenoxy)-pyrimidin-4-yl]-1,3-benzodioxol-5-sulfonamide. The last-named compound was converted into N-[5-(2-chloro-5-methoxy-phenoxy)-6-(2-methylsulphanyl-ethoxy)-pyrimidin-4-yl]-1,3-benzodioxol-5-sulfonamide as described in the preparation of the starting material in Example 47.

EXAMPLE 50

A solution of 0.11 g of sodium in 3.0 ml of ethylene glycol was heated to 110° C. with 0.265 g of 4-tert-butyl-N-[6-chloro-5-(2-methoxy-phenoxy)-2-(thiophen)-2-yl-pyrimidin-4-yl]-benzenesulfonamide, cooled for a further 4 hours, poured on to ice and adjusted to pH 3 with 1M tartaric acid. The suspension obtained was extracted with ethyl acetate, the organic extracts were combined, washed with water, dried with sodium sulfate and concentrated under reduced pressure. The residue was chromatographed on silica gel with $CH_2Cl_2$-ethyl acetate 9:1 and yielded 4-tert-butyl-N-[6-(2-hydroxy-ethoxy)-5-(2-methoxyphenoxy)-2-(thiophen-2-yl)-pyrimidin-4-yl]-benzenesulphonamide as a white foam. MS: M+ =555.

The starting material was prepared as follows:

a) A solution of 5.17 g of Na in 200 ml of abs. methanol was treated with 21.15 g of diethyl (o-methoxyphenoxy)malonate and 16.2 g of thiophene-2-carboxamidine hydrochloride and the suspension was stirred at room temperature overnight and evaporated under reduced pressure. The residue was taken up in 1N NaOH, the alkaline solution was acidified with 1N HCl, the precipitate was filtered off under suction, washed thoroughly with water and dried in a high vacuum at 80° C. The 5-(o-methoxyphenoxy)-2-(2-thienyl)-4,6-dihydroxy-pyrimidine of m.p. >250° C. (dec.) was used in the next step without further purification.

b) A suspension of 4.6 g of 5-(o-methoxyphenoxy)-2-(2-thienyl)-4,6-dihydroxy-pyrimidine, 4.7 ml of N,N-diisopropyl-N-ethylamine and 6.4 g of $PCl_5$ was boiled at reflux for 20 hours. The mixture was then evaporated under reduced pressure and the residue was poured on to ice and extracted with ethyl acetate. The combined extracts were washed with water, dried and evaporated in a vacuum. The residue was chromatographed on silica gel with toluene and yielded 4,6-dichloro-5-(2-methoxyphenoxy)-2-(thiophen-2-yl)-pyrimidine, m.p. 118°–120° C.

c) A solution of 0.353 g of 4,6-dichloro-5-(2-methoxyphenoxy)-2-(thiophen-2-yl)-pyrimidine in 5 ml of DMSO was heated to 150° C. with 0.376 g of p-tert-butylbenzenesulphonamide for 30 minutes. The solution was concentrated in a high vacuum and the oily residue was poured on to ice, made acid (pH=3) and the suspension was extracted with ethyl acetate. The organic extracts were combined, washed with water, dried over sodium sulfate and concentrated under reduced pressure. The residue was chromatographed on silica gel with toluene-ethyl acetate 9:1 and yielded 4-tert-butyl-N-[6-chloro-5-(2-methoxyphenoxy)-2-(thiophen-2-yl)-pyrimidin-4-yl]-benzenesulphonamide as a white foam.

EXAMPLE 51

In an analogous manner to Example 50, from 4-tert-butyl-N-[6-chloro-5-(2-methoxy-phenoxy)-2-(thiophen-3-yl)pyrimidin-4-yl]-benzenesulfonamide and ethylene glycol Na, there was obtained 4-tert-butyl-N-[6-(2-hydroxy-ethoxy)-5-(2-methoxy-phenoxy)-2-(thiophen-3-yl)-pyrimidin-4-yl]-benzenesulfonamide, m.p. 152°–153° C. (from toluene).

The 4-tert-butyl-N-[6-chloro-5-(2-methoxy-phenoxy)-2-(thiophen-3-yl)-pyrimidin-4-yl]-benzenesulfonamide (foam) was prepared starting from thiophene-3-carboxamidine hydrochloride via rac-5-(2-methoxy-phenoxy)-2-(thiophen-3-yl)3,4,5,6-tetrahydro-pyrimidine-4,6-dione (solid of m.p. >250° C.) and 4,6-dichloro-5-(2-methoxy-phenoxy)-2-(thiophen-3-yl)-pyrimidine (m.p. 98°–99° C.).

EXAMPLE 52

In analogy to Example 50, from 4-tert-butyl-N-[6-chloro-2-(furan-2-yl)-5-(2-methoxy-phenoxy)-pyrimidinyl-4-yl]-benzenesulfonamide and ethylene glycol Na, there was obtained 4-tert-butyl-N-[2-(furan-2-yl)-6-(2-hydroxy-ethoxy)-5-(2-methoxyphenoxy)-pyrimidin-4-yl]-bezenesulfonamide as an amorphous solid.

The 4-tert-butyl-N-[6-chloro-2-(furan-2yl)-5-(2-methoxy-phenoxy)-pyrimidin-4-yl]-benzenesulfonamide (foam) was prepared starting from furan-2-carboxamidine hydrochloride via rac-2-(furan-2-yl)-5-(2methoxy-phenoxy)-pyrimidine-4,6-dione (solid with a decomposition point of 255°–258° C.) and 4,6-dichloro-2-(furan-2-yl)-5-(2-methoxy-phenoxy)-pyrimidine.

EXAMPLE 53

In analogy to Example 50, from 4-tert-butyl-N-[6-chloro-2-furan-3-yl-5-(2-methoxy-phenoxy)-pyrimidin-4-yl]-benzenesulfonamide and ethylene glycol Na, there was obtained 4-tert-butyl-N-[2-(furan-3-yl)-6-(2-hydroxy-ethoxy)-5-(2-methoxyphenoxy)-pyrimidin-4-yl]-benzenesulfonamide as a solid of m.p. 120°–122° C. (from toluene/n-hexane).

The 4-tert-butyl-N-[6-chloro-2-(furan-3-yl)-5-(2-methoxy-phenoxy)-pyrimidin-4-yl]-benzenesulfonamide (foam) was prepared starting from furan-3-carboxamidine hydrochloride via rac-2-(furan-3-yl)-5-(2-methoxy-phenoxy)-4,6-dioxo-1,4,5,6-tetrahydro-pyrimidine (solid with a m.p. of more than 300° C. with decomposition) and 4,6-dichloro-2-(furan-3-yl)-5-(2-methoxy-phenoxy)-pyrimidine.

EXAMPLE 54

In analogy to Example 50, from 4-tert-butyl-N-[6-chloro-5-(2-methoxy-phenoxy)-2-(pyridin-2-yl)-pyrimidin-4-yl]-benzenesulfonamide and ethylene glycol Na, there was obtained 4-tert-butyl-N-[6-(2-hydroxy-ethoxy)-5-(2-methoxy-phenoxy)-2-(pyridin-2-yl)-pyrimidin-4-yl]-benzenesulfonamide as a solid with a m.p. above 250° C. (from ethyl acetate).

The 4-tert-butyl-N-[6-chloro-5-(2-methoxy-phenoxy)-2-(pyridin-2-yl)-pyrimidin-4-yl]-benzenesulfonamide (m.p. 197°–198° C. from isopropyl ether) was prepared starting from pyridine-2-carboxamidine hydrochloride via 5-(2-methoxy-phenoxy)-2-(pyridin-2-yl)pyrimidine- 4,6-diol and 4,6-dichloro-5-(2-methoxy-phenoxy)-2-(pyridin-2-yl)-pyrimidine, m.p. 122°–123° C.

EXAMPLE 55

In analogy to Example 50, from 4-tert-butyl-N-[6-chloro-5-(2-methoxy-phenoxy)-2-(pyridin-4-yl)-pyrimidin-4-yl]-benzenesulfonamide and ethylene glycol Na, there was obtained 4-tert-butyl-N-[6-(2-hydroxy-ethoxy)-5-(2-methoxy-phenoxy)-2-(pyridin-4-yl)-pyrimidin-4-yl]-benzenesulfonamide as a solid of m.p. 166°–167° C. from acetone-ether.

The 4-tert-butyl-N-[6-chloro-5-(2-methoxy-phenoxy)-2-(pyridin-4-yl)-pyrimidin-4-yl]-benzenesulfonamide potassium (1:1), m.p. 193°–196° C. from H$_2$O, was prepared starting from pyridine-4-carboxamidine hydrochloride via 5-(2-methoxyphenoxy)-2-(pyridin-4-yl)-pyrimidine-4,6-diol and 4,6-dichloro-5-(2-methoxyphenoxy)-2-(pyridin-4-yl)-pyrimidine, m.p. 173°–176° C.

EXAMPLE 56

In analogy to Example 50, from 4-tert-butyl-N-[6-chloro-5-(2-methoxy-phenoxy)-2-(pyridin-3-yl)-pyrimidin-4-yl]-benzenesulfonamide and ethylene glycol Na there was obtained 4-tert-butyl-N-[6-(2-hydroxy-ethoxy)-5-(2-methoxy-phenoxy)-2-(pyridin-3-yl)-pyrimidin-4-yl]-benzenesulfonamide K as a foam. MS: (M+H)+ = 551.2.

The 4-tert-butyl-N-[6-chloro-5-(2-methoxy-phenoxy)-2-(pyridin-3-yl)-pyrimidin-4-yl]-benzenesulfonamide was prepared starting from pyridine-3-carboxamidine hydrochloride via rac-5-(2-methoxy-phenoxy)-2-(pyridin-3-yl)-tetrahydro-1H-pyrimidine-4,6-dione and 4,6-dichloro-5-(2-methoxy-phenoxy)-2-(pyridin-3-yl)-pyrimidine (m.p. 164°–165° C.).

EXAMPLE 57

A suspension of 525 mg of 4-tert-butyl-N-[6-chloro-5-(2-methoxy-phenoxy)-2-(pyridin-2-yl)-pyrimidin-4-yl]benzenesulfonamide in 1 ml of glacial acetic acid was treated with 2.5 ml of 40% peracetic acid and slowly heated to reflux. After 2 minutes the mixture was cooled, evaporated under reduced pressure and the residue was recrystallized from ethyl acetate. There was obtained 2-[4-(4-tert-butyl-phenylsulphonylamino)-6-chloro-5-(2-methoxy-phenoxy)-pyrimidin-2-yl]-pyridine 1-oxide of m.p. 201°–202° C. (with decomposition).

EXAMPLE 58

216 mg of 2-[4-(4-tert-butyl-phenylsulphonylamino)-6-chloro-5-(2-methoxy-phenoxy)-pyrimidin-2-yl]-pyridine 1-oxide were added to a solution of 46 mg of Na in pure ethylene glycol and the solution which slowly resulted was heated at 80° C. overnight. The solution was poured into aqueous acetic acid, the precipitate was extracted with ethyl acetate, triturated with ether and filtered off under suction. There was obtained 2-[4-(4-tert-butyl-phenylsulphonylamino)-6-(2-hydroxy-ethoxy)-5-(2-methoxy-phenoxy)-pyrimidin-2-yl]-pyridine 1-oxide as an amorphous mass which was dried in a high vacuum at 40° C. MS: (M+H)+ = 567.4.

EXAMPLE 59

In analogy to Example 57, from 4-tert-butyl-N-[6-chloro-5-(2-methoxy-phenoxy)-2-(pyridin-4-yl)-pyrimidinyl-4-yl]benzenesulfonamide and peracetic acid, there was obtained 4-[4-(4-tert-butyl-phenylsulphonylamino)-6-chloro-5-(2-methoxyphenoxy)-pyrimidin-2-yl]-pyridine 1-oxide, m.p. 247°–249° C. (from CH$_2$Cl$_2$ and isopropyl ether).

EXAMPLE 60

In analogy to Example 58, from 4-[4-(4-tert-butyl-phenylsulphonylamino)-6-chloro-5-(2-methoxy-phenoxy)-pyrimidin-2-yl]-pyridine 1-oxide and Na ethylene glycolate in ethylene glycol, there was obtained 4-[4-(4-tert-butyl-phenylsulphonylamino)-6-(2-hydroxy-ethoxy)-5-(2-methoxy-phenoxy)-pyrimidin-2-yl]pyridine 1-oxide as an amorphous mass. MS: (M+H)+ = 567.4, (M+Na)+ = 589.4.

EXAMPLE 61

In analogy to Example 50, from 4-tert-butyl-N-[6-chloro-2-(2-methoxy-ethyl)-5-(2-methoxy-phenoxy)-pyrimidin-4-yl]-benzenesulfonamide and ethylene glycol Na, there was obtained 4-tert-butyl-N-[6-(2-hydroxy-ethoxy)-2-[2-(hydroxy-ethoxy)ethyl]-5-(2-methoxy-phenoxy)-pyrimidin-4-yl]-benzenesulfonamide. MS: M+ = 562. The corresponding sodium salt (prepared according to usual methods) is a white solid which was dried in a high vacuum.

The 4-tert-butyl-N-[6-chloro-2-(2-methoxy-ethyl)-5-(2-methoxy-phenoxy)-pyrimidin-4-yl]-benzenesulfonamide was prepared starting from methoxy-propionamidine hydrochloride via 2-(2-methoxy-ethyl)-5-(o-methoxyphenoxy)-4,6-(1H,5H)-pyrimidinedione and 4,6-dichloro-2-(2-methoxy-ethyl)-5-(2-methoxy-phenoxy)-pyrimidine.

EXAMPLE 62

In analogy to Example 50, from 4-tert-butyl-N-[6-chloro-2-cyclopropyl-5-(2-methoxy-phenoxy)-pyrimidin-4-yl]-benzenesulfonamide and ethylene glycol Na, there was obtained 4-tert-butyl-N-[2-cyclopropyl-6-(2-hydroxy-ethoxy)-5-(2-methoxyphenoxy)-pyrimidin-4-yl]-benzenesulfonamide as a foam. MS: M+ = 513.

The 4-tert-butyl-N-[6-chloro-2-cyclopropyl-5-(2-methoxy-phenoxy)-pyrimidin-4-yl]-benzenesulfonamide was prepared starting from cyclopropyl-formamidine hydrochloride via rac-2-cyclopropyl-5-(2-methoxy-phenoxy)-1H-pyrimidine-4,6-dione (m.p. 243°–244° C.) and 4,6-dichloro-2-cyclopropyl-5-(2-methoxy-phenoxy)pyrimidine (m.p. 80°–82° C.).

EXAMPLE 63

In analogy to Example 50, from 4-tert-butyl-N-[6-chloro-2-ethyl-5-(2-methoxy-phenoxy)-pyrimidin-4-yl]-benzenesulfonamide and ethylene glycol Na, there was obtained 4-tert-butyl-N-[2-ethyl-6-(2-hydroxy-ethoxy)-5-(2-methoxy-phenoxy)pyrimidin-4-yl]-benzenesulfonamide as a foam.

The 4-tert-butyl-N-[6-chloro-2-ethyl-5-(2-methoxyphenoxy)-pyrimidin-4-yl]-benzenesulfonamide was prepared starting from propionamidine hydrochloride via rac-2-ethyl-5-(2-methoxy-phenoxy)-1H-pyrimidine-4,6-dione (m.p. 265° C. with decomposition) and 4,6-dichloro-2-ethyl-5-(2-methoxy-phenoxy)-pyrimidine (m.p. 70°–71° C.).

EXAMPLE 64

In analogy to Example 50, from 4-tert-butyl-N-[6-chloro-2-isopropyl-5-(2-methoxy-phenoxy)-pyrimidin-4-yl]-benzenesulfonamide and ethylene glycol Na, there was obtained 4-tert-butyl-N-[6-(2-hydroxy-ethoxy)-2-isopropyl-5-(2-methoxy-phenoxy)-pyrimidin-4-yl]-benzenesulfonamide as a solid.

The 4-tert-butyl-N-[6-chloro-2-isopropyl-5-(2-methoxy-phenoxy)-pyrimidin-4-yl]-benzenesulfonamide was prepared starting from isopropionamidine hydrochloride via rac-2-iso-propyl-5-(2-methoxy-phenoxy)-1,4,5,6-tetrahydro-pyrimidine-4,6-dione and 4,6-dichloro-2-isopropyl-5-(2-methoxy-phenoxy)-pyrimidine (m.p. 70°–72° C.).

EXAMPLE 65

In analogy to Example 50, from 4-chloro-N-[6-chloro-5-(5-fluoro-2-methoxy-phenoxy)-pyrimidin-4-yl]-benzenesulphonamide and ethylene glycol Na, there was obtained 4-chloro-N-[3-(5-fluoro-2-methoxy-phenoxy)-6-(2-hydroxy-ethoxy)-pyrimidin-4-yl]-benzenesulfonamide, m.p. 152°–154° C. (from CH₃CN and iso-propyl ether).

The 4-chloro-N-[6-chloro-5-(5-fluoro-2-methoxy-phenoxy)-pyrimidin-4-yl]-benzenesulfonamide (m.p. 169°–171° C.) was prepared from 4,6-dichloro-5-(5-fluoro-2-methoxy-phenoxy)-pyrimidine and 4-chlorobenzenesulfonamide K.

EXAMPLE 66

In analogy to Example 50, from N-[6-chloro-5-(5-fluoro-2-methoxy-phenoxy)-pyrimidin-4-yl]-4-trifluoromethyl-benzenesulfonamide and sodium ethylene glycolate, there was obtained N-[5-(5-fluoro-2-methoxy-phenoxy)-6-(2-hydroxy-ethoxy)pyrimidin-4-yl]-4-trifluoromethyl-benzenesulfonamide, m.p. 154°–155° C. (from isopropyl ether).

The N-[6-chloro-5-(5-fluoro-2-methoxy-phenoxy)-pyrimidin-4-yl]-4-trifluoromethyl-benzenesulfonamide (m.p. 185°–186° C.) was prepared from 4,6-dichloro-5-(5-fluoro-2-methoxy-phenoxy)-pyrimidine and 4-trifluoromethylbenzenesulfonamide K.

EXAMPLE 67

In analogy to Example 50, but with a reaction temperature of 100° C., from 4-tert-butyl-N-[6-chloro-5-(2-methoxy-phenoxy)-2-(pyrimidin-2-yl)-pyrimidin-4-yl]-benzenesulphonamide and sodium ethylene glycolate in ethylene glycol, there was obtained 4-tert-butyl-N-[6-(2-hydroxy-ethoxy)-5-(2-methoxy-phenoxy)-2-(pyrimidin-2-yl)-pyrimidin-4-yl]-benzenesulphonamide as a solid. Sodium salt: m.p. 195°–198° C.

The 4-tert-butyl-N-[6-chloro-5-(2-methoxy-phenoxy)-2-pyrimidin-2-yl)-pyrimidin-4-yl]-benzenesulfonamide was prepared starting from pyrimidine-2-carboxamidine hydrochloride via rac-5-(2-methoxy-phenoxy)-2-(pyrimidin-2-yl)tetrahydro-pyrimidine-4,6-dione and 4,6-dichloro-5-(2-methoxy-phenoxy)-2,2′-bipyrimidine.

EXAMPLE 68

In analogy to Example 50, from 4-tert-butyl-N-[6-chloro-5-(3-methoxy-phenoxy)-2,2′-bipyrimidin-4-yl]-benzenesulphonamide and Na ethylene glycolate in ethylene glycol, there was obtained 4-tert-butyl-N-[6-(2-hydroxy-ethoxy)-5-(3-methoxy-phenoxy)-2,2′-bipyrimidin-4-yl]-benzenesulfonamide as a solid.

The 4-tert-butyl-N-[6-chloro-5-(3-methoxy-phenoxy)-2,2′-bipyrimidin-4-yl]-benzenesulfonamide was prepared starting from rac-5-(3-methoxy-phenoxy)-2-(pyrimidin-2-yl)-1,4,5,6-tetrahydro-pyrimidine-4,6-dione via 4,6-dichloro-5-(3-methoxy-phenoxy)-2,2′-bipyrimidinyl.

EXAMPLE 69

In analogy to Example 50, from 4-tert-butyl-N-[6-chloro-5-(4-fluoro-2-methoxy-phenoxy)-2,2′-bipyrimidin-4-yl]-benzenesulfonamide and Na ethylene glycolate in ethylene glycol, there was obtained 4-tert-butyl-N-[5-(4-fluoro-2-methoxy-phenoxy)-6-(2-hydroxyethoxy)-2,2′-bipyrimidin-4-yl]-benzenesulfonamide, m.p. 161°–163° C.

The 4-tert-butyl-N-[6-chloro-5-(4-fluoro-2-methoxy-phenoxy)-2,2′-bipyrimidin-4-yl]-benzenesulfonamide (m.p. 225°–227° C.) was prepared starting from diethyl (4-fluoro-2-methoxy-phenoxy)malonate via 5-(4-fluoro-2-methoxy-phenoxy)-2,2′-bipyrimidine-4,6-diol (decomposition point >131° C.) and 4,6-dichloro-5-(4-fluoro-2-methoxy-phenoxy)-2,2′-bipyrimidine (m.p. 179°–180° C.).

EXAMPLE 70

In analogy to Example 50, from 4-tert-butyl-N-[6-chloro-5-(4-fluoro-2-methoxy-phenoxy)-2-methyl-pyrimidin-4-yl]-benzenesulfonamide and Na ethylene glycolate in ethylene glycol, there was obtained 4-tert-butyl-N-[5-(4-fluoro-2-methoxy-phenoxy)-6-(2-hydroxy-ethoxy)-2-methyl-pyrimidin-4-yl]-benzenesulfonamide, m.p. 141°–142° C. (from CH₂Cl₂-isopropyl ether).

The 4-tert-butyl-N-[6-chloro-5-(4-fluoro-2-methoxy-phenoxy)-2-methyl-pyrimidin-4-yl]-benzenesulfonamide (m.p. 164°–165° C.) was prepared starting from diethyl (4-fluoro-2-methoxy-phenoxy)malonate via rac-5-(4-fluoro-2-methoxy-phenoxy)-2-methyl-1,4,5,6-tetrahydropyrimidine-4,6-dione and 4,6-dichloro-5-(4-fluoro-2-methoxy-phenoxy)-2-methylpyrimidine (m.p. 129°–130° C.).

EXAMPLE 71

In analogy to Example 50, from 4-tert-butyl-N-[6-chloro-5-(4-fluoro-2-methoxy-phenoxy)-pyrimidin-4-yl]-benzenesulphonamide and Na ethylene glycolate in ethylene glycol there was obtained 4-tert-butyl-N-[5-(4-fluoro-2-methoxy-phenoxy)-6-(2-hydroxy-ethoxy)-pyrimidin-4-yl]-benzenesulfonamide, m.p. 143°–144° C. (from CH₂Cl₂-isopropyl ether).

The 4-tert-butyl-N-[6-chloro-5-(4-fluoro-2-methoxy-phenoxy)-pyrimidin-4-yl]-benzenesulfonamide (m.p. 146°–147° C.) was prepared starting from diethyl (4-fluoro-2-methoxy-phenoxy)malonate via rac-5-(4-fluoro-2-methoxy-phenoxy)-1,4,5,6-tetrahydro-pyrimidine-4,6-dione and 4,6-dichloro-5-(4-fluoro-2-methoxy-phenoxy)pyrimidine (m.p. 100°–101° C.).

EXAMPLE 72

In analogy to Example 50, from N-[6-chloro-5-(5-fluoro-2-methoxy-phenoxy)-pyrimidin-4-yl]-4-isopropyl-benzenesulphonamide and Na ethylene glycolate in ethylene glycol, there was obtained N-[5-(5-fluoro-2-methoxy-phenoxy)-6-(2-hydroxy-ethoxy)-pyrimidin-4-yl]-4-isopropyl-benzenesulfonamide, m.p. 131°–132° C. (from isopropyl ether).

EXAMPLE 73

In analogy to Example 50, from N-[6-chloro-5-(5-fluoro-2-methoxy-phenoxy)-pyrimidin-4-yl]-4-tert-butyl-benzenesulfonamide and Na ethylene glycolate in ethylene glycol, there was obtained N-[5-(5-fluoro-2-methoxy-phenoxy)-6-(2-hydroxy-ethoxy)-pyrimidine-4- yl]-4-tert-butyl-benzenesulfonamide, m.p. 126°–127° C. (from isopropyl ether).

The N-[6-chloro-5-(5-fluoro-2-methoxy-phenoxy)-pyrimidin-4-yl]-4-isopropyl-benzenesulfonamide, m.p. 138°–139° C., was prepared starting from diethyl (5-fluoro-2-methoxy-phenoxy)malonate via rac-5-(5-fluoro-2-methoxy-phenoxy)-tetrahydro-pyrimidine-4,6-dione, 4,6-dichloro-5-(5-fluoro-2-methoxy-phenoxy)-pyrimidine (m.p. 98°–100° C.) and N-[6-chloro-5-(5-fluoro-2-methoxy-phenoxy)-pyrimidin-4-yl]-4-tert-butyl-benzenesulfonamide (m.p. 163°–164° C.).

EXAMPLE 74

In analogy to Example 50, from 4-tert-butyl-N-[6-chloro-5-(2-fluoro-6-methoxy-phenoxy)-pyrimidin-4-yl]-benzenesulphonamide and Na ethylene glycolate in ethylene glycol, there was obtained 4-tert-butyl-N-[5-(2-fluoro-6-methoxy)-6-(2-hydroxy-ethoxy)-pyrimidin-4-yl]-benzenesulfonamide, m.p. 158°–159° C. (from $CH_2Cl_2$-isopropyl ether).

The 4-tert-butyl-N-[6-chloro-5-(2-fluoro-6-methoxy-phenoxy)-pyrimidin-4-yl]-benzesulfonamide (m.p. 181°–182° C.) was prepared starting from diethyl 2-(2-fluoro-6-methoxy-phenoxy)malonate via rac-5-(2-fluoro-6-methoxy-phenoxy)-1,4,5,6-tetrahydro-pyrimidine-4,6-dione and 4,6-dichloro-5-(2-fluoro-6-methoxy-phenoxy)-pyrimidine (m.p. 78°–79° C.).

EXAMPLE 75

In analogy to Example 50, from 4-tert-butyl-N-[6-chloro-5-(3-methoxy-phenoxy)-2-(thiophen-2-yl)-pyrimidin-4-yl]-benzenesulfonamide and Na ethylene glycolate in ethylene glycol, there was obtained 4-tert-butyl-N-[6-(2-hydroxy-ethoxy)-5-(3-methoxy-phenoxy)-2-(thiophen-2-yl)-pyrimidin-4-yl]-benzenesulfonamide, m.p. 159°–161° C. (toluene/n-hexane).

The 4-tert-butyl-N-[6-chloro-5-(3-methoxy-phenoxy)-2-(thiophene-2-yl)-pyrimidin-4-yl]-benzenesulfonamide (m.p. 206°–207° C.) was prepared starting from rac-5-(3-methoxy-phenoxy)-2-(thiophen-2-yl)-3,4,5,6-tetrahydropyrimidine-4,6-dione via 4,6-dichloro-5-(3-methoxy-phenoxy)-2-(thiophen-2-yl)-pyrimidine (m.p. 120°–121° C.).

EXAMPLE 76

In analogy to Example 50, from 4-tert-butyl-N-[6-chloro-2-(2-methoxy-ethyl)-5-(3-methoxy-phenoxy)-pyrimidin-4-yl]-benzenesulfonamide and Na ethylene glycolate in ethylene glycol, there were obtained, after separation by chromatography on silica gel, 4-tert-butyl-N-[6-(2-hydroxy-ethoxy)-2-(2-methoxy-ethyl)-5-(3-methoxy-phenoxy)-pyrimidin-4-yl]-benzenesulfonamide and 4-tert-butyl-N-[6-(2-hydroxy-ethoxy)-2-[2-(2-hydroxy-ethoxy)ethyl]-5-(3-methoxy-phenoxy)-pyrimidin-4-yl]-benzenesulfonamide.

The 4-tert-butyl-N-[6-chloro-2-(2-methoxy-ethyl)-5-(3-methoxy-phenoxy)-pyrimidin-4-yl]-benzenesulfonamide was prepared starting from methoxypropionamidine hydrochloride via 2-(2-methoxy-ethyl)-5-(3-methoxy-phenoxy)-1,4,5,6-tetrahydro-pyrimidine-4,6-dione and 4,6-dichloro-2-(2-chloro-ethyl)-5-(3-methoxy-phenoxy)-pyrimidine.

EXAMPLE 77

In analogy to Example 50, from p-tert-butyl-N-[6-chloro-5-(o-methoxy-phenoxy)-2-methyl-4-pyrimidinyl]-benzenesulfonamide and (S)-2,2-dimethyl-1,3-dioxolane-4-methanol Na, there was obtained (S)-4-tert-butyl-N-[6-(2,2-dimethyl-1,3-dioxolan-4-ylmethoxy)-5-(2-methoxy-phenoxy)-2-methyl-pyrimidin-4-yl]-benzenesulfonamide, m.p. 124°–125° C. (from n-hexane).

EXAMPLE 78

A solution of 1.85 g of (S)-4-tert-butyl-N-[6-(2,2-dimethyl-1,3-dioxolan-4-ylmethoxy)-5-(2-methoxy-phenoxy)-2-methylpyrimidin-4-yl]-benzenesulfonamide in EtOH (15 ml) was treated with 3 ml of conc. HCl and heated to 50° C. for 2 minutes. After evaporation, the residue was extracted with ether and yielded (R)-4-tert-butyl-N-[6-(2,3-dihydroxy-propoxy)-5-(2-methoxy-phenoxy)-2-methyl-pyrimidin-4-yl]-benzenesulfonamide as a foam.

EXAMPLE 79

From N-[6-chloro-5-(5-fluoro-2-methoxy-phenoxy)-pyrimidin-4-yl]-4-tert-butyl-benzenesulfonamide and (R)-2,2-dimethyl-1,3-dioxolane-4-methanol Na, there was obtained (R)-4-tert-butyl-N-[5-(5-fluoro-2-methoxy-phenoxy)-6-(2,2-dimethyl-1,3-dioxolan-4-ylmethoxy)-pyrimidin-4-yl]-benzenesulphonamide (m.p. >86° C.). Treatment with dilute hydrochloric acid yielded (S)-4-tert-butyl-N-5-(fluoro-2-methoxy-phenoxy)-6-(2,3-dihydroxy-propoxy)-pyrimidin-4-yl]-benzenesulfonamide as a foam.

EXAMPLE 80

From N-[6-chloro-5-(5-fluoro-2-methoxy-phenoxy)-pyrimidin-4-yl]-4-tert-butyl-benzenesulfonamide and (S)-2,2-dimethyl-1,3-dioxolane-4-methanol sodium salt, there was obtained (S)-4-tert-butyl-N-[5-(5-fluoro-2-methoxy-phenoxy)-6-(2,2-dimethyl-1,3-dioxolan-4-ylmethoxy)-pyrimidin-4-yl]-benzenesulfonamide (m.p. >86° C.). Treatment with dilute HCl yielded (R)-4-tert-butyl-N-[5-(5-fluoro-2-methoxy-phenoxy)-6-(2,3-dihydroxy-propoxy)-pyrimidin-4-yl]-benzenesulfonamide as a foam.

EXAMPLE 81

From 4-tert-butyl-N-[6-chloro-5-(2-methoxy-phenoxy)-2-(thiophen-2-yl)-pyrimidin-4-yl]-benzenesulfonamide and (S)-2,2-dimethyl-1,3-dioxolane-4-methanol sodium salt, there was obtained 4-tert-butyl-N-[6-[(S)-1,3-dioxolan-4-ylmethoxy]-5-(2-methoxy-phenoxy)-2-(thiophen-2-yl)-pyrimidin-4-yl]-benzenesulfonamide as a foam. Treatment with dilute hydrochloric acid in dioxan yielded (R)-4-tert-butyl-N-[6-(2,3-dihydroxy-propoxy)-5-(2-methoxy-phenoxy)-2-(thiophen-2-yl)-pyrimidin-4-yl]-benzenesulfonamide as a foam.

EXAMPLE 82

From 4-tert-butyl-N-[6-chloro-5-(2-methoxy-phenoxy)-2-(thiophen-2-yl)-pyrimidin-4-yl]-benzenesulfonamide and (R)-2,2-dimethyl-1,3-dioxolan-4-methanol sodium salt, there was obtained 4-tert-butyl-N-[6-(R)-1,3-dioxolan-4-ylmethoxy]-5-(2-methoxy-phenoxy)-2-(thiophen-2-yl)-pyrimidin-4-yl]-benzenesulfonamide and therefrom with dilute HCl in dioxan, there was obtained (S)-4-tert-butyl-N-[6-(2,3-dihydroxy-propoxy)-5-(2-methoxy-phenoxy)-2-(thiophen-2-yl)-pyrimidin-4-yl]-benzenesulfonamide.

EXAMPLE 83

From 4-tert-butyl-N-[6-chloro-5-(2-methoxy-phenoxy)-2-(thiophen-3-yl)-pyrimidin-4-yl]-benzenesulfonamide and (R)-2,2-dimethyl-1,3-dioxolane-4-methanol sodium salt, there was obtained (R)-4-tert-butyl-N-[6-(2,2-dimethyl-1,3-dioxolan-4-ylmethoxy)-5-(2-methoxy-phenoxy)-2-(thiophen-3-yl)-pyrimidin-4-yl]-benzenesulfonamide and therefrom with dilute HCl in dioxan there was obtained 4-tert-butyl-N-[6-[(S)-2,3-dihydroxy-propoxy]-5-(2-methoxy-phenoxy)-2-(thiophen-3-yl)-pyrimidin-4-yl]-benzenesulfonamide.

EXAMPLE 84

From 4-tert-butyl-N-[6-chloro-5-(2-methoxy-phenoxy)-2-(thiophen-3-yl)-pyrimidin-4-yl]-benzenesulfonamide and (S)-2,2-dimethyl-1,3-dioxolane-4-methanol sodium salt there was obtained (S)-4-tert-butyl-N-[(2,2-dimethyl-1,3-dioxolan-4-ylmethoxy)-5-(2-methoxy-phenoxy)-2-(thiophen-3-yl)-pyrimidin-4-yl]-benzenesulfonamide and therefrom with dilute HCl in dioxan there was obtained 4-tert-butyl-N-[6-[(R)-2,3-dihydroxy-propoxy]-5-(2-methoxy-phenoxy)-2-(thiophen-3-yl)-pyrimidin-4-yl]-benzensulfonamide.

EXAMPLE 85

From 4-tert-butyl-N-[6-chloro-2-(furan-3-yl)-5-(2-methoxy-phenoxy)-pyrimidin-4-yl]-benzenesulfonamide and (S)-2,2-dimethyl-1,3-dioxolane-4-methanol sodium salt, there was obtained (S)-4-tert-butyl-N-[6-(2,2-dimethyl-1,3-dioxolan-4-ylmethoxy)-2-(furan-3-yl)-5-(2-methoxy-phenoxy)-pyrimidin-4-yl]-benzenesulfonamide and therefrom with dilute HCl in dioxan there was obtained (R)-4-tert-butyl-N-[2-(furan-3-yl)-6-(2,3-dihydroxy-propoxy)-5-(2-methoxy-phenoxy)-pyrimidin-4-yl]-benzenesulfonamide.

EXAMPLE 86

From 4-tert-butyl-N-[6-chloro-2-(furan-3-yl)-5-(2-methoxy-phenoxy)-pyrimidin-4-yl]-benzenesulfonamide and (R)-2,2-dimethyl-1,3-dioxolane-4-methanol sodium salt, there was obtained (R)-4-tert-butyl-N-[6-(2,2-dimethyl-1,3-dioxolan-4-ylmethoxy)-2-(furan-3-yl)-5-(2-methoxy-phenoxy)-pyrimidin-4-yl]-benzenesulfonamide and therefrom with dilute HCl in dioxan there was obtained (S)-4-tert-butyl-N-[2-(furan-3-yl)-6-(2,3-dihydroxy-propoxy)-5-(2-methoxy-phenoxy)-pyrimidin-4-yl]-benzenesulfonamide.

EXAMPLE 87

By reaction of p-t-butyl-N-[6-(2-hydroxy-ethoxy)-5-(m-methoxy-phenoxy)-4-pyrimidinyl]benzenesulfonamide and 3-methyl-5-isoxazole carboxylic acid in the presence of dimethylamino pyridine and dicyclohexylcarbodiimide in methylene chloride, there was obtained 3-methylisoxazole-5-carboxylic acid 2-[6-(4-t-butylbenzenesulfonamino)-5-(3-methoxy-phenoxy)pyrimidin-4-yloxy]ethyl ester as a white solid.

EXAMPLE 88

In analogy to Example 87 employing indole-2-carboxylic acid, there was obtained indole-2-carboxylic acid 2-[6-(4-t-butylbenzenesulfonamino)-5-(3-methoxy-phenoxy)pyrimidin-4-yloxy]ethyl ester.

EXAMPLE 89

To a solution of 391.5 mg of 6-[2-(t-butyl-dimethylsilyloxy)ethoxy]-5-(2-methoxyphenoxy)pyrimidin-4-yl-amine in 20 ml of acetonitril, there were added 200 mg of NaH (60%) and the reaction mixture was stirred for one hour at room temperature. 400 mg of (2-methoxy-5-chlorosulfonyl)phenoxyacetic acid ethyl ester were added. The reaction mixture was stirred for 3.5 hours at room temperature, poured on ice and extracted with ethyl acetate. The organic phase was dried and evaporated. Chromatography on silica gel with methylene chloride/methanol (120:1) afforded 175 mg of 4-[6-[2-(t-butyl-dimethylsilyloxy)ethoxy]-5-(2-methoxyphenoxy)pyrimidin--4-yl-aminosulfonyl]-2-methoxyphenoxy acetic acid ethyl ester as a white foam. That compound was dissolved in 6 ml of acetonitril and 1 ml of aqueous hydrogen fluoride (40%) were added slowly at 0° C. The reaction mixture was stirred for 30 minutes at 0° C. and for 90 minutes at room temperature, poured on ice/2N KHCO₃ solution and extracted with methylene chloride. The organic phase was dried and evaporated and the residue chromatographed on silica gel with methylene chloride/methanol (10:1). There was obtained 5-[N-[6-(2-hydroxyethoxy)-5-(2-methoxyphenoxy)-pyrimidin-4-yl]aminosulfonyl]-2-methoxyphenoxy acetic acid ethyl ester as a white solid.

The starting material was prepared as follows:

Ca. 105 ml of ammonia were passed into a solution of 7 g of 4,6-dichloro-5-(o-methoxyphenoxy)pyrimidine in 140 ml of ethanol at −78° C. The reaction mixture was stirred for 15 hours at −78° C. and for 50 hours at room temperature and then concentrated. The residue was distributed between ethyl acetate and water and the organic phase worked up. There were obtained 6.45 g of 4-amino-6-chloro-5-(o-methoxyphenoxy)pyrimidine as white crystals.

2.3 g of the above obtained compound were added to a solution of 250 mg of sodium in 40 ml of ethylene glycol at 50° C. The solution was heated to 100° C. for 12 hours, distributed between half-saturated aqueous NH₄Cl solution and methylene chloride and the organic phase worked up. There were obtained 2.49 g 2-[6-amino-5-(o-methoxyphenoxy)-4-pyrimidinyl]-1-ethanol as white crystals.

To a solution of 2.5 g of the above obtained compound in 100 ml of methylene chloride, 2.74 g of dimethylamino pyridine and 3.39 g of t-butyl dimethylchlorosilane were added and the mixture was stirred at room temperature for 48 hours. A further 1.35 g of dimethylamino pyridine and 1.65 g of t-butyl dimethylchlorosilane were then added and the reaction mixture stirred for another 18 hours at room temperature. The reaction mixture was filtered, the filtrate concentrated and the residue distributed between half-saturated aqueous NH₄Cl solution and ethyl acetate. Work-up of the organic phase yielded 2.78 g of 6-[2-(t-butyl-dimethylsilyloxy)-5-(2-methoxyphenoxy)pyrimidin-4-yl amine as a white solid.

EXAMPLE A

Tablets containing the following ingredients can be prepared in a conventional manner:

| Ingredients | Per tablet |
| --- | --- |
| Compound of formula I | 10.0–100.0 mg |
| Lactose | 125.0 mg |
| Maize starch | 75.0 mg |
| Talc | 4.0 mg |
| Magnesium stearate | 1.0 mg |

EXAMPLE B

Capsules containing the following ingredients can be prepared in a conventional manner:

| Ingredients | Per capsule |
|---|---|
| Compound of formula I | 25.0 mg |
| Lactose | 150.0 mg |
| Maize starch | 20.0 mg |
| Talc | 5.0 mg |

EXAMPLE C

Injectable solutions can have the following composition:

| Compound of formula I | 3.0 mg |
|---|---|
| Gelatine | 150.0 mg |
| Phenol | 4.7 mg |
| Water for injection solutions | ad 1.0 ml |

EXAMPLE D 500 mg of compound of formula I are suspended in 3.5 ml of Myglyol 812 and 0.08 g of benzyl alcohol. This suspension is filled into a container having a dosage valve. 5.0 g of Freon 12 under pressure are filled into the container through the valve. The Freon is dissolved in the Myglyol-benzyl alcohol mixture by shaking. This spray container contains about 100 single dosages which can be applied individually.

We claim:

1. A compound of the formula

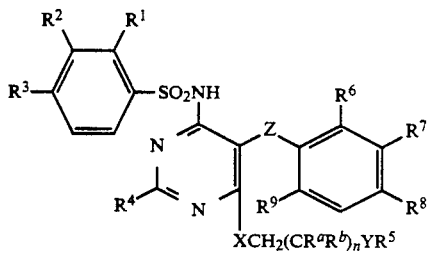

I wherein
$R^1$ is hydrogen, lower-alkyl, lower alkoxy, lower-alkylthio, halogen or trifluoromethyl;
$R^2$ is hydrogen, halogen, lower-alkoxy, trifluoromethyl or $-OCH_2COOR^a$; and
$R^3$ is hydrogen, halogen, lower-alkyl, lower-alkylthio, trifluoromethyl, $C_3-C_8$ cycloalkyl, lower-alkoxy or trifluoromethoxy; or
$R^2$ and $R^3$ together signify butadienyl, methylenedioxy, ethylenedioxy or isopropylidenedioxy;
$R^4$ is hydrogen, lower-alkyl, $C_3-C_8$ cycloalkyl, trifluoromethyl, lower-alkoxy, lower alkylthio, lower-alkylthio-lower-alkyl, hydroxy-lower-alkyl, hydroxy-lower alkoxy, lower-alkoxy-lower alkyl, hydroxy-lower-alkoxy-lower-alkyl, hydroxy-lower-alkoxy-lower-alkoxy, lower-alkylsulphinyl, lower-alkylsulphonyl, 2-methoxy-3-hydroxypropoxy, 2-hydroxy-3-phenylpropyl, amino-lower alkyl, lower-alkylamino-lower-alkyl, di-lower-alkylamino-lower-alkyl, amino, lower-alkylamino, di-lower-alkylamino, unsubstituted phenyl amino, phenylamino substituted with halogen, lower-alkyl, lower alkoxy-carboxyl or trifluoromethyl, unsubstituted phenyl, phenyl substituted with halogen, lower alkyl, lower-alkoxy-carboxyl or trifluoromethyl, unsubstituted phenylthio, phenylthio substituted with halogen, lower-alkyl, lower alkoxy carboxyl or trifluoromethyl, unsubstituted phenoxy, phenoxy substituted with halogen, lower alkyl, lower-alkoxy-carboxyl or trifluoromethyl, unsubstituted phenyl-lower alkyl, phenyl-lower-alkyl substituted with halogen, lower-alkyl, lower-alkoxy-carboxyl or trifluoromethyl, unsubstituted heterocyclyl selected from 2-furyl, 3-furyl, pyrimidyl, 2-pyridyl, 3-pyridyl, 4-pyridyl, pyridyl N-oxide, 1,2-diazinyl, 1,4-diazinyl, morpholino, 2-thienyl, 3-thienyl, isoxazolyl, oxazolyl, imidazolyl, pyrrolyl, benzofuranyl, benzothienyl, indolyl, purinyl, quinolyl, isoquinolyl and quinazolyl or heterocyclyl as defined above substituted by lower alkyl, lower alkoxy, halogen, phenyl, or phenyl-lower alkyl;
$R^5$ is hydrogen, lower-alkyl, lower-alkanoyl, benzoyl, heterocyclylcarbonyl wherein the heterocyclyl is selected from unsubstituted 2-furyl, 3-furyl, pyrimidyl, 2-pyridyl, 3-pyridyl, 4-pyridyl, pyridyl N-oxide, 1,2-diazinyl, 1,4-diazinyl, morpholino, 2-thienyl, 3-thienyl, isoxazolyl, oxazolyl, imidazolyl, pyrrolyl, benzofuranyl, benzothienyl, indolyl, purinyl, quinolyl, isoquinolyl and quinazolyl or heterocyclyl as defined above substituted by lower alkyl, lower alkoxy, halogen, phenyl, phenyl-lower alkyl, heterocyclyl methyl wherein the heterocyclyl is selected from 2-furyl, 3-furyl, pyrimidyl, 2-pyridyl, 3-pyridyl, 4-pyridyl, pyridyl N-oxide, 1,2-diazinyl, 1,4-diazinyl, morpholino, 2-thienyl, 3-thienyl, isoxazolyl, oxazolyl, imidazolyl, pyrrolyl, benzofuranyl, benzothienyl, indolyl, purinyl, quinolyl, isoquinolyl and quinazolyl or heterocyclyl as defined above substituted by lower alkyl, lower alkoxy, halogen, phenyl or phenyl-lower alkyl, or tetrahydro-pyran-2-yl;
$R^6$ to $R^9$ are hydrogen, halogen, trifluoromethyl, lower-alkyl, lower-alkoxy, lower-alkylthio, hydroxy, hydroxymethyl, cyano, carboxyl, formyl, methylsulphinyl, methylsulphonyl, methylsulphonyloxy or lower-alkyloxycarbonyloxy; or
$R^7$ together with $R^6$ or $R^8$ signify butadienyl, methylenedioxy, ethylenedioxy or isopropylidenedioxy;
Z is $-O-$, $-S-$, vinylene, $-CO-$, $OCHR^{10}-$ or $-SCHR^{10}$;
$R^{10}$ is hydrogen or lower alkyl;
X and Y each independently are O, S or NH; or $YR^5$ is lower-alkylsulphinyl;
$R^a$, $R^b$, $R^c$ and $R^d$ each independently are hydrogen or lower-alkyl; or $R^c$ and $R^d$ together are methylene, ethylene or isopropylidene; and
n is 1, 2 or 3,
or a stereoisomer or salt thereof.

2. The compound of claim 1, wherein
$R^1$ is hydrogen lower-alkyl, lower alkoxy, lower-alkylthio, halogen or trifluoromethyl;
$R^2$ is hydrogen, halogen, lower-alkoxy or trifluoromethyl; and
$R^3$ is hydrogen, halogen, lower-alkyl, lower-alkylthio, trifluoromethyl, $C_3-C_8$ cycloalkyl, lower-alkoxy or trifluoromethoxy; or
$R^2$ and $R^3$ together signify butadienyl, methylenedioxy,
$R^4$ is hydrogen, lower-alkyl, trifluoromethyl, lower-alkoxy, lower alkylthio, lower-alkylthio-lower-alkyl, hydroxy-lower-alkyl, amino-lower alkyl, lower-alkylamino-lower-alkyl, di-lower-alkylamino-lower-alkyl, amino, lower-alkylamino, di-lower-alkylamino, unsubstituted phenyl amino, phenylamino substituted with halogen, lower-alkyl, lower alkoxy-carboxyl or trifluoromethyl, unsubstituted phenyl, phenyl substituted with halogen, lower alkyl, lower-alkoxycarboxyl or trifluoromethyl, unsubstituted phenylthio, phenylthio substituted with halogen, lower-alkyl, lower alkoxy carboxyl or trifluoromethyl, unsubstituted phenoxy, phenoxy substituted with halogen, lower alkyl, lower-alkoxy-carboxyl or trifluoromethyl, unsubstituted phenyl-lower alkyl, phenyl-lower-alkyl substituted with halogen, lower-alkyl, lower-alkoxy-carboxyl or trifluoromethyl, unsubstituted heterocyclyl selected from 2-furyl, 3-furyl, pyrimidyl, 2-pyridyl, 3-pyridyl, 4-pyridyl, pyridyl N-oxide, 1,2-diazinyl, 1,4-diazinyl, morpholino, 2-thienyl, 3-thienyl, isoxazolyl, oxazolyl, imidazolyl, pyrrolyl, benzofuranyl, benzothienyl, indolyl, purinyl, quinolyl, isoquinolyl and quinazolyl or heterocyclyl as defined above substituted by lower alkyl, lower alkoxy, halogen, phenyl or phenyl-lower alkyl;

$R^5$ is hydrogen, lower-alkanoyl, benzoyl or tetrahydropyran-2-yl;

$R^6$ to $R^9$ are hydrogen, halogen, trifluoromethyl, lower-alkyl, lower-alkoxy, lower-alkylthio, hydroxy, hydroxymethyl, cyano, carboxyl, formyl, methylsulphinyl, methylsulphonyl, methylsulphonyloxy or lower-alkoxy-carbonyloxy; or $R^7$ together with $R^6$ or $R^8$ signify butadienyl or —OCH$_2$O—;

Z is —O—, —S—, vinylene, —CO—, OCHR$^{10}$— or —SCHR$^{10}$;

$R^{10}$ is hydrogen or lower-alkyl;

X and Y each independently are O, S or NH;

$R^a$ and $R^b$ are hydrogen; and n is 1, 2 or 3 or a stereoisomer or salt thereof.

3. A compound according to claim 1, wherein Z is —O—.

4. A compound according to claim 2, wherein $R^6$ is lower-alkoxy and $R^7$, $R^8$ and $R^9$ are hydrogen.

5. A compound according to claim 2, wherein $R^6$ and $R^8$ are hydrogen, $R^7$ is lower-alkoxy and $R^9$ is halogen.

6. A compound according to claim 1, wherein $R^4$ is hydrogen, 2-pyrimidinyl, 2- or 3-furyl, 2- or 3-thienyl, morpholino or p-methoxyphenyl.

7. A compound according to claim 1, wherein YR$^5$ is hydroxy, lower-alkoxysulphinyl or furoyloxy.

8. A compound according to claim 3, selected from the group consisting of p-t-butyl-N-[6-(2-hydroxyethoxy)-5-(o-methoxyphenoxy)-4-pyrimidinyl]benzenesulfonamide, N-[6-(2-hydroxyethoxy)-5-(o-methoxyphenoxy)-4-pyrimidinyl]-p-isopropylbenzenesulfonamide, p-t-butyl-N-[6-(2-hydroxyethoxy)-5-(o-tolyloxy)-4-pyrimidinyl]benzenesulfonamide, p-t-butyl-N-[6-(2-hydroxyethoxy)-5-(o-chlorophenyloxy)-4-pyrimidinyl]benzenesulfonamide, N-[6-(2-hydroxyethoxy)-5-(o-chlorophenoxy)-4-pyrimidinyl]-p-isopropylbenzenesulfonamide, p-t-butyl-N-[6-(2-hydroxyethoxy)-5-(m-methoxyphenoxy)-4-pyrimidinyl]benzenesulfonamide, p-t-butyl-N-[6-(2-hydroxyethoxy)-5-phenoxy-4-pyrimidinyl]benzenesulfonamide, p-t-butyl-N-[6-(2-hydroxyethoxy)-5-(p-methoxyphenoxy)-4-pyrimidinyl]benzenesulfonamide, p-t-butyl-N-[6-(2-hydroxyethoxy)-5-(o-ethoxyphenoxy)-4-pyrimidinyl]benzenesulfonamide, p-(2,2-dimethylpropyl)-N-[6-(2-hydroxyethoxy)-5-(o-methoxyphenoxy)-4-pyrimidinyl]benzenesulfonamide, p-isopropyl-N-[6-(2-hydroxyethoxy)-2-methyl-5-(m-methoxyphenoxy)-4-pyrimidinyl]benzenesulfonamide, N-[6-(2-hydroxyethoxy)-5-(o-methoxyphenoxy)-2-phenyl-4-pyrimidinyl]-p-isopropylbenzenesulfonamide, N-[6-(2-hydroxyethoxy)-5-(2,4,6-trichlorophenoxy)-4-pyrimidinyl]-p-isopropylbenzenesulfonamide, N-[6-(2-hydroxyethoxy)-6-(2,4,6-trichlorophenoxy)-4-pyrimidinyl]-o-toluenesulfonamide, N-[6-(2-hydroxyethoxy)-5-(2,4,6-trichlorophenoxy)-4-pyrimidinyl]-2,4-xylenesulfonamide, p-t-butyl-N-[6-(2-hydroxyethoxy)-5-[(2-methoxy-p-tolyl)oxy]-4-pyrimidinyl]benzenesulfonamide, N-[5-(2-methoxy-4-methylphenoxy)-6-(2-hydroxyethoxy)-4-pyrimidinyl]-p-iso-propylbenzenesulfonamide, N-[5-(2-methoxy-4-methylphenoxy)6-(2-hydroxyethoxy)-4-pyrimidinyl]-o-ethylbenzenesulfonamide, p-tert-butyl-N-[6-(2-hydroxyethoxy)-5-(o-methoxyphenoxy)-2-methyl-4-pyrimidinyl]benzenesulfonamide, N-[6-(2-hydroxyethoxy)-5-(o-methoxyphenoxy)-2-methyl-4-pyrimidinyl]-p-isopropylbenzenesulfonamide, N-[6-(2-hydroxyethoxy)-5-(o-methoxyphenoxy)-2-(trifluoromethyl)-4-pyrimidinyl]-p-isopropylbenzenesulfonamide, p-tert-butyl-N-[6-(2-hydroxyethoxy)-5-(o-methoxyphenoxy)-2-(trifluoromethyl)-4-pyrimidinyl]benzenesulfonamide, N-[5-(1,3-benzodioxol-5-yloxy)-6-(2-hydroxyethoxy)-4-pyrimidinyl]-p-tertbutylbenzenesulfonamide, N-[5-(1,3-benzodioxol-5-yloxy)-6-(2-hydroxyethoxy)-4-pyrimidinyl]-p-isopropylbenzenesulfonamide, N-[6-(2-hydroxyethoxy)-5-(o-methoxyphenoxy)-4-pyrimidinyl]-o-methoxybenzenesulfonamide, p-tert-butyl-N-[6-(4-hydroxybutoxy)-5-(o-methoxyphenoxy)-2-methyl-4-pyrimidinyl]benzenesulfonamide, N-[6-(2-hydroxyethoxy)-5-(2-naphthyloxy)-4-pyrimidinyl]-p-isopropylbenzenesulfonamide, N-[6-(2-hydroxyethoxy)-5-(2-naphthyloxy)-4-pyrimidinyl]-p-tert-butylbenzenesulfonamide, N-[6-(2-hydroxyethoxy)-5-(o-methoxyphenoxy)-2-propyl-4-pyrimidinyl]-p-isopropylbenzenesulfonamide, p-tert-butyl-N-[6-(2-hydroxyethoxy)-5-(o-methoxyphenoxy)-2-propyl-4-pyrimidinyl]benzenesulfonamide, α,α,α-trifluoro-N-[6-(2-hydroxyethoxy)-5-(o-methoxyphenoxy)-2-methyl-4-pyrimidinyl]-p-toluenesulfonamide, p-chloro-N-[6-(2-hydroxyethoxy)-5-(o-methoxyphenoxy)-2-methyl-4-pyrimidinyl]benzenesulfonamide, N-[6-(2-hydroxyethoxy)-5-(o-methoxyphenoxy)-2-methyl-4-pyrimidinyl]-p-(trifluoromethoxy)benzenesulfonamide, o-ethyl-N-[6-(2-hydroxyethoxy)-5-(o-methoxyphenoxy)-2-methyl-4-pyrimidinyl]benzenesulfonamide, N-[6-(2-hydroxyethoxy)-5-(o-methoxyphenoxy)-2-methyl-4-pyrimidinyl]-p-toluenesulfonamide,
p-tert-butyl-N-[6-(3-hydroxypropoxy)-5-(o-methoxyphenoxy)-2-methyl-4-pyrimidinyl]benzenesulfonamide,
p-t-butyl-N-[6-(2-hydroxyethoxy)-5-[(o-methylthio)phenoxy]-4-pyrimidinyl]benzenesulfonamide,
p-t-butyl-N-[6-(2-hydroxyethoxy)-5-(o-methoxyphenoxy)-2-phenyl-4-pyrimidinyl]benzenesulfonamide,
N-[2-amino-6-(2-hydroxyethoxy)-5-(o-methoxyphenoxy)-4-pyrimidinyl]-p-t-butylbenzenesulfonamide,
p-t-butyl-N-[6-(2-hydroxyethoxy)-2-methyl-5-[o-(methylthio)phenoxy]-4-pyrimidinyl]benzenesulfonamide and
p-t-butyl-N-[6-(2-hydroxyethoxy)-2-methyl-5-[o-(R,S-methylsulphinyl)phenoxy]-4-pyrimidinyl]benzenesulfonamide.

9. A compound according to claim 3, selected from the group consisting of:
4-tert-butyl-N-[5-(2-chloro-5-methoxy-phenoxy)-6-(2-hydroxy-ethoxy)-2-methyl-pyrimidin-4-yl]-benzene-sulfonamide,
4-tert-butyl-N-[5-(2-chloro-5-methoxy-phenoxy)-6-[2-(3-furoyloxy)ethoxy]-2-methyl-pyrimidin-4-yl]-benzene-sulfonamide,
4-tert-butyl-N-[6-(2-hydroxy-ethoxy)-5-(2-methoxyphenoxy)-2-(thiophen-2-yl)-pyrimidin-4-yl]-benzene-sulfonamide,
4-tert-butyl-N-[6-(2-hydroxy-ethoxy)-5-(2-methoxyphenoxy)-2-(thiophen-3-yl)-pyrimidin-4-yl]-benzene-sulfonamide,
4-tert-butyl-N-[2-(furan-2-yl)-6-(2-hydroxy-ethoxy)-5-(2-methoxy-phenoxy)-pyrimidin-4-yl]-benzenesulfonamide,
4-tert-butyl-N-[2-(furan-3-yl)-6-(2-hydroxy-ethoxy)-5-(2-methoxy-phenoxy)-pyrimidin-4-yl]-benzenesulfonamide,
4-tert-butyl-N-[6-(2-hydroxy-ethoxy)-5-(2-methoxyphenoxy)-2-(pyridin-2-yl)-pyrimidin-4-yl]-benzenesulfonamide,
4-tert-butyl-N-[6-(2-hydroxy-ethoxy)-5-(2-methoxyphenoxy)-2-(pyridin-4-yl)-pyrimidin-4-yl]-benzenesulfonamide,
4-tert-butyl-N-[6-(2-hydroxy-ethoxy)-5-(2-methoxyphenoxy)-2-(pyridin-3-yl)-pyrimidin-4-yl]-benzenesulfonamide,
2-[4-(4-tert-butyl-phenylsulphonylamino)-6-(2-hydroxy-ethoxy)-5-(2-methoxy-phenoxy)-pyrimidin-2-yl]-pyridine 1-oxide,
4-[4-(4-tert-butyl-phenylsulphonylamino)-6-(2-hydroxy-ethoxy)-5-(2-methoxy-phenoxy)-pyrimidin-2-yl]-pyridine 1-oxide,
4-tert-butyl-N-[6-(2-hydroxy-ethoxy)-2-[2-(2-hydroxy-ethoxy)ethyl]-5-(2-methoxy-phenoxy)-pyrimidin-4-yl]-benzenesulfonamide,
4-tert-butyl-N-[2-cyclopropyl-6-(2-hydroxy-ethoxy)-5-(2-methoxy-phenoxy)-pyrimidin-4-yl]-benzenesulfonamide,
4-tert-butyl-N-[2-ethyl-6-(2-hydroxy-ethoxy)-5-(2-methoxy-phenoxy)-pyrimidin-4-yl]-benzenesulfonamide,
4-tert-butyl-N-[6-(2-hydroxy-ethoxy)-2-isopropyl-5-(2-methoxy-phenoxy)-pyrimidin-4-yl]-benzenesulfonamide,
4-chloro-N-[3-(5-fluoro-2-methoxy-phenoxy)-6-(2-hydroxy-ethoxy)-pyrimidin-4-yl]-benzenesulfonamide,
N-[5-(5-fluoro-2-methoxy-phenoxy)-6-(2-hydroxy-ethoxy)-pyrimidin-4-yl]-4-trifluoromethyl-benzenesulfonamide,
4-tert-butyl-N-[6-(2-hydroxy-ethoxy)-5-(3-methoxyphenoxy)-2,2'-bipyrimidin-4-yl]-benzenesulfonamide,
4-tert-butyl-N-[5-(4-fluoro-2-methoxy-phenoxy)-6-(2-hydroxy-ethoxy)-2,2'-bipyrimidin-4-yl]-benzenesulfonamide,
4-tert-butyl-N-[5-(4-fluoro-2-methoxy-phenoxy)-6-(2-hydroxy-ethoxy)-2-methyl-pyrimidin-4-yl]-benzene-sulfonamide,
4-tert-butyl-N-[5-(4-fluoro-2-methoxy-phenoxy)-6-(2-hydroxy-ethoxy)-pyrimidin-4-yl]-benzenesulfonamide,
N-[5-(5-fluoro-2-methoxy-phenoxy)-6-(2-hydroxy-ethoxy)-pyrimidin-4-yl]-4-isopropyl-benzenesulfonamide,
N-[5-(5-fluoro-2-methoxy-phenoxy)-6-(2-hydroxy-ethoxy)-pyrimidin-4-yl]-4-tert-butyl-benzenesulfonamide,
4-tert-butyl-N-[5-(2-fluoro-6-methoxy)-6-(2-hydroxy-ethoxy)-pyrimidin-4-yl]-benzenesulfonamide,
4-tert-butyl-N-[6-(2-hydroxy-ethoxy)-5-(3-methoxyphenoxy)-2-(thiophen-2-yl)-pyrimidin-4-yl]-benzenesulfonamide,
4-tert-butyl-N-[6-(2-hydroxy-ethoxy)-2-(2-methoxyethyl)-5-(3-methoxy-phenoxy)-pyrimidin-4-yl]-benzenesulfonamide,
4-tert-butyl-N-[6-(2-hydroxy-ethoxy)-2-[2-(2-methoxy-ethoxy)ethyl]-5-(3-methoxy-phenoxy)-pyrimidin-4-yl]-benzenesulfonamide,
3-methylisoxazole-5-carboxylic acid 2-[6-(4-t-butyl-benzenesulfonamino)-5-(3-methoxyphenoxy)-pyrimidin-4-yloxy]-ethyl ester,
indole-2-carboxylic acid 2-[6-(4-t-butylbenzenesulfonamino)-5-(3-methoxyphenoxy)pyrimidin-4-yloxy]ethyl ester, and
5-[N-[6-(2-hydroxyethoxy)-5-(2-methoxyphenoxy)-pyrimidin-4-yl]aminosulfonyl]-2-methoxyphenoxy acetic acid ethyl ester.

10. The compound, N-[6-(2-hydroxyethoxy)-5-(O-methoxyphenoxy)-2-methyl-4-pyrimidinyl]-2-naphthylsulfonamide.

11. (S)-4-tert-Butyl-N-[6-(2,3-dihydroxy-propyloxy)-5-(2-methoxy-phenoxy)-2-(4-methoxyphenyl)-pyrimidin-4-yl]-benzenesulfonamide.

12. (RS)-4-tert-Butyl-N-[5-(2-chloro-5-methoxyphenoxy)-2-ethyl-6-(2-methylsulphinyl-ethoxy)-pyrimidin-4-yl]-benzenesulfonamide.

13. (RS)-N-[5-(2-Chloro-5-methoxy-phenoxy)-6-(2-methylsulphinyl-ethoxy)-pyrimidin-4-yl]-1,3-benzodioxol-5-sulfonamide.

14. 4-tert-Butyl-N-[6-(2-hydroxy-ethoxy)-5-(2-methoxy-phenoxy)-2-(pyrimidin-2-yl)-pyrimidin-4-yl]-benzenesulfonamide.

15. A compound according to claim 2, wherein Z is or vinylene.

16. A compound according to claim 15, selected from the group consisting of
2-[[5-[(E/Z)-styryl]-6-p-toluenesulphonamido-4-pyrimidinyl]oxy]ethyl acetate and
N-[6-(2-hydroxyethoxy)-5-([E/Z]-styryl]-4-pyrimidinyl]-p-toluenesulfonamide.

17. A compound of the formula $$\text{II}$$

[Structure II: benzene ring with R¹, R², R³ substituents, connected via SO₂NH to a vinyl group with N, R⁴, N, and Z-linked second benzene ring with R⁶, R⁷, R⁸, R⁹ and Hal]

wherein

R¹ is hydrogen, lower-alkyl, lower alkoxy, lower-alkylthio, halogen or trifluoromethyl;

R² is hydrogen, halogen, lower-alkoxy, trifluoromethyl or —OCH₂COOR$^a$; and

R³ is hydrogen, halogen, lower-alkyl, lower-alkylthio, trifluoromethyl, $C_3$-$C_8$ cycloalkyl, lower-alkoxy or trifluoromethoxy; or R² and R³ together signify butadienyl, methylenedioxy, ethylenedioxy or isopropylidenedioxy;

R⁴ is hydrogen, lower-alkyl, $C_3$-$C_8$ cycloalkyl, trifluoromethyl, lower-alkoxy, lower alkylthio, lower-alkylthio-lower-alkyl, hydroxy-lower-alkyl, hydroxy-lower alkoxy, lower-alkoxy-lower alkyl, hydroxy-lower-alkoxy-lower-alkyl, hydroxy-lower-alkoxy-lower-alkoxy, lower-alkylsulphinyl, lower-alkylsulphonyl, 2-methoxy-3-hydroxypropoxy, 2-hydroxy-3-phenylpropyl, amino-lower alkyl, lower-alkylamino-lower-alkyl, di-lower-alkylamino-lower-alkyl, amino, lower-alkylamino, di-lower-alkylamino, unsubstituted phenyl amino, phenylamino substituted with halogen, lower-alkyl, lower alkoxycarboxyl or trifluoromethyl, unsubstituted phenyl, phenyl substituted with halogen, lower alkyl, lower-alkoxy-carboxyl or trifluoromethyl, unsubstituted phenylthio, phenylthio substituted with halogen, lower-alkyl, lower alkoxy carboxyl or trifluoromethyl, unsubstituted phenoxy, phenoxy substituted with halogen, lower alkyl, lower-alkoxy-carboxyl or trifluoromethyl, unsubstituted phenyl-lower alkyl, phenyl-lower-alkyl substituted with halogen, lower-alkyl, lower-alkoxy-carboxyl or trifluoromethyl, unsubstituted heterocyclyl selected from 2-furyl, 3-furyl, pyrimidyl, 2-pyridyl, 3-pyridyl, 4-pyridyl, pyridyl N-oxide, 1,2-diazinyl, 1,4-diazinyl, morpholino, 2-thienyl, 3-thienyl, isoxazolyl, oxazolyl, imidazolyl, pyrrolyl, benzofuranyl, benzothienyl, indolyl, purinyl, quinolyl, isoquinolyl and quinazolyl or heterocyclyl as defined above substituted by lower alkyl, lower alkoxy, halogen, phenyl or phenyl-lower alkyl;

R⁵ is hydrogen, lower-alkyl, lower alkanoyl, benzoyl, heterocyclylcarbonyl wherein the heterocyclyl is selected from unsubstituted 2-furyl, 3-furyl, pyrimidyl, 2-pyridyl, 3-pyridyl, 4-pyridyl, pyridyl N-oxide, 1,2-diazinyl, 1,4-diazinyl, morpholino, 2-thienyl, 3-thienyl, isoxazolyl, oxazolyl, imidazolyl, pyrrolyl, benzofuranyl, benzothienyl, indolyl, purinyl, quinolyl, isoquinolyl and quinazolyl or heterocyclyl as defined above substituted by lower alkyl, lower alkoxy, halogen, phenyl, phenyl-lower alkyl, heterocyclyl methyl wherein the heterocyclyl is selected from 2-furyl, 3-furyl, pyrimidyl, 2-pyridyl, 3-pyridyl, 4-pyridyl, pyridyl N-oxide, 1,2-diazinyl, 1,4-diazinyl, morpholino, 2-thienyl, 3-thienyl, isoxazolyl, oxazolyl, imidazolyl, pyrrolyl, benzofuranyl, benzothienyl, indolyl, purinyl, quinolyl, isoquinolyl and quinazolyl or heterocyclyl as defined above substituted by lower alkyl, lower alkoxy, halogen, phenyl or phenyl-lower alkyl, or tetrahydropyran-2-yl;

Z is —O—, —S—, vinylene, —CO—, OCHR¹⁰— or —SCHR¹⁰;

R¹⁰ is hydrogen or lower-alkyl;

R$^a$ and R$^b$ each independently are hydrogen or lower-alkyl; and n is 1, 2 or 3.

18. A pharmaceutical composition comprising a compound of the formula $$\text{I}$$

[Structure I: benzene ring with R¹, R², R³ substituents, connected via SO₂NH to a vinyl group with N, R⁴, N, and Z-linked second benzene ring with R⁶, R⁷, R⁸, R⁹, and XCH₂(CR$^a$R$^b$)$_n$YR⁵]

wherein

R¹ is hydrogen, lower-alkyl, lower alkoxy, lower-alkylthio, halogen or trifluoromethyl;

R² is hydrogen, halogen, lower-alkoxy, trifluoromethyl or —OCH₂COOR$^a$; and

R³ is hydrogen, halogen, lower-alkyl, lower-alkylthio, trifluoromethyl, $C_3$-$C_8$ cycloalkyl, lower-alkoxy or trifluoromethoxy; or R² and R³ together are butadienyl, methylenedioxy, ethylenedioxy or isopropylidenedioxy;

R⁴ is hydrogen, lower-alkyl, $C_3$-$C_8$ cycloalkyl, trifluoromethyl, lower-alkoxy, lower alkylthio, lower-alkylthio-lower-alkyl, hydroxy-lower-alkyl, hydroxy-lower alkoxy, lower-alkoxy-lower alkyl, hydroxy-lower-alkoxy-lower-alkyl, hydroxy-lower-alkoxy-lower-alkoxy, lower-alkylsulphinyl, lower-alkylsulphonyl, 2-methoxy-3-hydroxyproxy, 2-hydroxy-3-phenylpropyl, amino-lower alkyl, lower-alkylamino-lower-alkyl, di-lower-alkylamino-lower-alkyl, amino, lower-alkylamino, di-lower-alkylamino, unsubstituted phenyl amino, phenylamino substituted with halogen, lower-alkyl, lower alkoxycarboxyl or trifluoromethyl, unsubstituted phenyl, phenyl substituted with halogen, lower alkyl, lower-alkoxy-carboxyl or trifluoromethyl, unsubstituted phenylthio, phenylthio substituted with halogen, lower-alkyl, lower alkoxy carboxyl or trifluoromethyl, unsubstituted phenoxy, phenoxy substituted with halogen, lower alkyl, lower-alkoxy-carboxyl or trifluoromethyl, unsubstituted phenyl-lower alkyl, phenyl-lower-alkyl substituted with halogen, lower-alkyl, lower-alkoxy-carboxyl or trifluoromethyl, unsubstituted heterocyclyl selected from 2-furyl, 3-furyl, pyrimidyl, 2-pyridyl, 3-pyridyl, 4-pyridyl, pyridyl N-oxide, 1,2-diazinyl, 1,4-diazinyl, morpholino, 2-thienyl, 3-thienyl, isoxazolyl, oxazolyl, imidazolyl, pyrrolyl, benzofuranyl, benzothienyl, indolyl, purinyl, quinolyl, isoquinolyl and quinazolyl or heterocyclyl as defined above substituted by lower alkyl, lower alkoxy, halogen, phenyl or phenyl-lower alkyl;

$R^5$ is hydrogen, lower-alkyl, lower alkanoyl, benzoyl, heterocyclylcarbonyl wherein the heterocyclyl is selected from unsubstituted 2-furyl, 3-furyl, pyrimidyl, 2-pyridyl, 3-pyridyl, 4-pyridyl, pyridyl N-oxide, 1,2-diazinyl, 1,4-diazinyl, morpholino, 2-thienyl, 3-thienyl, isoxazolyl, oxazolyl, imidazolyl, pyrrolyl, benzofuranyl, benzothienyl, indolyl, purinyl, quinolyl, isoquinolyl and quinazolyl or heterocyclyl as defined above substituted by lower alkyl, lower alkoxy, halogen, phenyl, phenyl-lower alkyl, heterocyclyl methyl wherein the heterocyclyl is selected from 2-furyl, 3-furyl, pyrimidyl, 2-pyridyl, 3-pyridyl, 4-pyridyl, pyridyl N-oxide, 1,2-diazinyl, 1,4-diazinyl, morpholino, 2-thienyl, 3-thienyl, isoxazolyl, oxazolyl, imidazolyl, pyrrolyl, benzofuranyl, benzothienyl, indolyl, purinyl, quinolyl, isoquinolyl and quinazolyl or heterocyclyl as defined above substituted by lower alkyl, lower alkoxy, halogen, phenyl or phenyl-lower alkyl, or tetrahydropyran-2-yl;

$R^6$ to $R^9$ are hydrogen, halogen, trifluoromethyl, lower-alkyl, lower-alkoxy, lower-alkylthio, hydroxy, hydroxymethyl, cyano, carboxyl, formyl, methylsulphinyl, methylsulphonyl, methylsulphonyloxy or lower-alkyloxy-carboyloxy; or $R^7$ together with $R^6$ or $R^8$ signify butadienyl, methylenedioxy, ethylenedioxy or isopropylidenedioxy;

is —O—, —S—, vinylene, —CO—, OCHR$^{10}$— or —SCHR$^{10}$;

$R^{10}$ is hydrogen or lower alkyl;

X and Y each independently are O, S or NH; or YR$^5$ is lower-alkylsulphinyl;

$R^a$, $R^b$, $R^c$ and $R^d$ each independently are hydrogen or lower-alkyl; or $R^c$ and $R^d$ together signify methylene, ethylene or isopropylidene; and n is 1, 2 or 3 or a stereoisomer or salt thereof and an inert carrier.

19. The pharmaceutical composition of claim 18, wherein $R^1$ is hydrogen, lower-alkyl, lower alkoxy, lower-alkylthio, halogen or trifluoromethyl;

$R^2$ is hydrogen, halogen, lower-alkoxy, trifluoromethyl;

$R^3$ is hydrogen, halogen, lower-alkyl, lower-alkylthio, trifluoromethyl, $C_3$-$C_8$ cycloalkyl, lower-alkoxy or trifluoromethoxy; or $R^2$ and $R^3$ together are butadienyl, methylenedioxy;

$R^4$ is hydrogen, lower-alkyl, trifluoromethyl, lower-alkoxy, lower alkylthio, lower-alkylthio-lower-alkyl, hydroxy-lower-alkyl, amino-lower alkyl, lower-alkylamino-lower-alkyl, di-lower-alkylamino-lower-alkyl, amino, lower-alkylamino, di-lower-alkylamino, unsubstituted phenyl amino, phenylamino substituted with halogen, lower-alkyl, lower alkoxy-carboxyl or trifluoromethyl, unsubstituted phenyl, phenyl substituted with halogen, lower alkyl, lower-alkoxy-carboxyl or trifluoromethyl, unsubstituted phenylthio, phenylthio substituted with halogen, lower-alkyl, lower alkoxy carboxyl or trifluoromethyl, unsubstituted phenoxy, phenoxy substituted with halogen, lower alkyl, lower-alkoxy-carboxyl or trifluoromethyl, unsubstituted phenyl-lower alkyl, phenyl-lower-alkyl substituted with halogen, lower-alkyl, lower-alkoxy-carboxyl or trifluoromethyl, unsubstituted heterocyclyl selected from 2-furyl, 3-furyl, pyrimidyl, 2-pyridyl, 3-pyridyl, 4-pyridyl, pyridyl N-oxide, 1,2-diazinyl, 1,4-diazinyl, morpholino, 2-thienyl, 3-thienyl, isoxazolyl, oxazolyl, imidazolyl, pyrrolyl, benzofuranyl, benzothienyl, indolyl, purinyl, quinolyl, isoquinolyl and quinazolyl or heterocyclyl as defined above substituted by lower alkyl, lower alkoxy, halogen, phenyl or phenyl-lower alkyl;

$R^5$ is hydrogen, lower-alkanoyl, benzoyl or tetrahydropyran-2-yl;

$R^6$ to $R^9$ are hydrogen, halogen, trifluoromethyl, lower-alkyl, lower-alkoxy, lower-alkylthio, hydroxy, hydroxymethyl, cyano, carboxyl, formyl, methylsulphinyl, methylsulphonyl, methylsulphonyloxy or lower-alkoxy-carboyloxy; or together with $R^6$ or $R^8$ signify butadienyl or —OCH$_2$O—;

Z is —O—, —S—, vinylene, —CO—, OCHR$^{10}$— or —SCHR$^{10}$;

$R^{10}$ is hydrogen or lower-alkyl;

X and Y each independently are O, S or NH;

$R^a$ and $R^b$ are hydrogen; and n is 1, 2 or 3 or a stereoisomer or salt thereof.

20. A method of treating disorders associated with endothelin activities comprising administering to a host in need of such treatment an effective amount of a compound of the formula

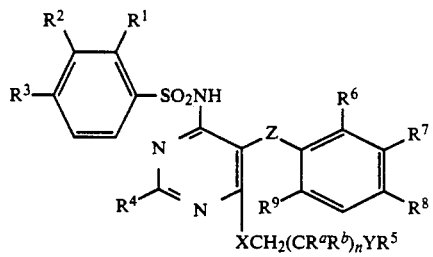

wherein $R^1$ is hydrogen, lower-alkyl, lower alkoxy, lower-alkylthio, halogen or trifluoromethyl;

$R^2$ is hydrogen, halogen, lower-alkoxy, trifluoromethyl or —OCH$_2$COOR$^a$;

$R^3$ is hydrogen, halogen, lower-alkyl, lower-alkylthio, trifluoromethyl, $C_3$-$C_8$ cycloalkyl, lower-alkoxy or trifluoromethoxy; or $R^2$ and $R^3$ together signify butadienyl, methylenedioxy, ethylenedioxy or isopropylidenedioxy;

$R^4$ is hydrogen, lower-alkyl, $C_3$-$C_8$ cycloalkyl, trifluoromethyl, lower-alkoxy, lower alkylthio, lower-alkylthio-lower-alkyl, hydroxy-lower-alkyl, hydroxy-lower alkoxy, lower-alkoxy-lower alkyl, hydroxy-lower-alkoxy-lower-alkyl, hydroxy-lower-alkoxy-lower-alkoxy, lower-alkylsulphinyl, lower-alkylsulphonyl, 2-methoxy-3-hydroxypropoxy, 2-hydroxy-3-phenylpropyl, amino-lower-alkyl, lower-alkylamino-lower-alkyl, di-lower-alkylamino-lower-alkyl, amino, lower-alkylamino, di-lower-alkylamino, unsubstituted phenyl amino, phenylamino substituted with halogen, lower-alkyl, lower alkoxy-carboxyl or trifluoromethyl, unsubstituted phenyl, phenyl substituted with halogen, lower alkyl, lower-alkoxy-carboxyl or trifluoromethyl, unsubstituted phenylthio, phenylthio substituted with halogen, lower-alkyl, lower alkoxy carboxyl or trifluoromethyl, unsubstituted phenoxy, phenoxy substituted with halogen, lower alkyl, lower-alkoxy-carboxyl or trifluoromethyl, unsubstituted phenyl-lower alkyl, phenyl-lower-alkyl substituted with halogen, lower-alkyl, lower-alkoxy-carboxyl or trifluoromethyl, unsubstituted heterocyclyl selected from 2-furyl, 3-furyl, pyrimidyl, 2-pyridyl, 3-pyridyl, 4-pyridyl, pyridyl N-oxide, 1,2-diazinyl, 1,4-diazinyl, morpholino, 2-thienyl, 3-thienyl, isoxazolyl, oxazolyl, imidazolyl, pyrrolyl, benzofuranyl, benzothienyl, indolyl, purinyl, quinolyl, isoquinolyl and quinazolyl or heterocyclyl as defined above substituted by lower alkyl, lower alkoxy, halogen, phenyl or phenyl-lower alkyl;

$R^5$ is hydrogen, lower-alkyl, lower-alkanoyl, benzoyl, heterocyclylcarbonyl wherein the heterocyclyl is selected from unsubstituted 2-furyl, 3-furyl, pyrimidyl, 2-pyridyl, 3-pyridyl, 4-pyridyl, pyridyl N-oxide, 1,2-diazinyl, 1,4-diazinyl, morpholino, 2-thienyl, 3-thienyl, isoxazolyl, oxazolyl, imidazolyl, pyrrolyl, benzofuranyl, benzothienyl, indolyl, purinyl, quinolyl, isoquinolyl and quinazolyl or heterocyclyl as defined above substituted by lower alkyl, lower alkoxy, halogen, phenyl, phenyl-lower alkyl, heterocyclyl methyl wherein the heterocyclyl is selected from 2-furyl, 3-furyl, pyrimidyl, 2-pyridyl, 3-pyridyl, 4-pyridyl, pyridyl N-oxide, 1,2-diazinyl, 1,4-diazinyl, morpholino, 2-thienyl, 3-thienyl, isoxazolyl, oxazolyl, imidazolyl, pyrrolyl, benzofuranyl, benzothienyl, indolyl, purinyl, quinolyl, isoquinolyl and quinazolyl or heterocyclyl as defined above substituted by lower alkyl, lower alkoxy, halogen, phenyl or phenyl-lower alkyl, or tetrahydro-pyran-2-yl;

$R^6$ to $R^9$ are hydrogen, halogen, trifluoromethyl, lower-alkyl, lower-alkoxy, lower-alkylthio, hydroxy, hydroxymethyl, cyano, carboxyl, formyl, methylsulphinyl, methylsulphonyl, methylsulphonyloxy or lower-alkyloxycarbonyloxy; or $R^7$ together with $R^6$ or $R^8$ signify butadienyl, methylenedioxy, ethylenedioxy or isopropylidenedioxy;

is —O—, —S—, vinylene, —CO—, OCHR$^{10}$— or —SCHR$^{10}$;

$R^{10}$ is hydrogen or lower-alkyl;

X and Y each independently are O, S or NH; or YR$^5$ is lower-alkylsulphinyl;

$R^a$, $R^b$, $R^c$ and $R^d$ each independently are hydrogen or lower-alkyl; or $R^c$ and $R^d$ together signify methylene, ethylene or isopropylidene; and n is 1, 2 or 3 or a stereoisomer or salt thereof.

21. The method of claim 20, wherein
$R^1$ is hydrogen, lower-alkyl, lower alkoxy, lower-alkylthio, halogen or trifluoromethyl;
$R^2$ is hydrogen, halogen, lower-alkoxy, trifluoromethyl;
$R^3$ is hydrogen, halogen, lower-alkyl, lower-alkylthio, trifluoromethyl, $C_3$–$C_8$ cycloalkyl, lower-alkoxy or trifluoromethoxy; or
$R^2$ and $R^3$ together are butadienyl or methylenedioxy;
$R^4$ is hydrogen, lower-alkyl, trifluoromethyl, lower-alkoxy, lower alkylthio, lower-alkylthio-lower-alkyl, hydroxy-lower-alkyl, amino-lower alkyl, lower-alkylamino-lower-alkyl, di-lower-alkylamino-lower-alkyl, amino, lower-alkylamino, di-lower-alkylamino, unsubstituted phenyl amino, phenylamino substituted with halogen, lower-alkyl, lower alkoxy-carboxyl or trifluoromethyl, unsubstituted phenyl, phenyl substituted with halogen, lower alkyl, lower-alkoxy-carboxyl or trifluoromethyl, unsubstituted phenylthio, phenylthio substituted with halogen, lower-alkyl, lower alkoxy carboxyl or trifluoromethyl, unsubstituted phenoxy, phenoxy substituted with halogen, lower alkyl, lower-alkoxy-carboxyl or trifluoromethyl, unsubstituted phenyl-lower alkyl, phenyl-lower-alkyl substituted with halogen, lower-alkyl, lower-alkoxy-carboxyl or trifluoromethyl, unsubstituted heterocyclyl selected from 2-furyl, 3-furyl, pyrimidyl, 2-pyridyl, 3-pyridyl, 4-pyridyl, pyridyl N-oxide, 1,2-diazinyl, 1,4-diazinyl, morpholino, 2-thienyl, 3-thienyl, isoxazolyl, oxazolyl, imidazolyl, pyrrolyl, benzofuranyl, benzothienyl, indolyl, purinyl, quinolyl, isoquinolyl and quinazolyl or heterocyclyl as defined above substituted by lower alkyl, lower alkoxy, halogen, phenyl or phenyl-lower alkyl;

$R^5$ is hydrogen, lower-alkanoyl, benzoyl or tetrahydropyran-2-yl;

$R^6$ to $R^9$ are hydrogen, halogen, trifluoromethyl, lower-alkyl, lower-alkoxy, lower-alkylthio, hydroxy, hydroxymethyl, cyano, carboxyl, formyl, methylsulphinyl, methylsulphonyl, methylsulphonyloxy or lower-alkoxycarbonyloxy; or $R^7$ together with $R^6$ or $R^8$ signify butadienyl or —OCH$_2$O—;

Z is —O—, —S—, vinylene, —CO—, OCHR$^{10}$— or —SCHR$^{10}$;

$R^{10}$ is hydrogen or lower-alkyl;

X and Y each independently are O, S or NH;

$R^a$ and $R^b$ are hydrogen; and n is 1, 2 or 3 or a stereoisomer or salt thereof.

22. The pharmaceutical composition of claim 18, wherein Z is —O—.

23. The pharmaceutical composition of claim 19, $R^6$ is lower-alkoxy and $R^7$, $R^8$ and $R^9$ are hydrogen.

24. The pharmaceutical composition of claim 19, wherein $R^6$ and $R^8$ are hydrogen, $R^7$ is lower-alkoxy and $R^9$ is halogen.

25. The pharmaceutical composition of claim 18, wherein $R^4$ is hydrogen, 2-pyrimidinyl, 2- or 3-furyl, 2- or 3-thienyl, morpholino or p-methoxyphenyl.

26. The method of claim 20, wherein the disorder is a circulatory disorder.

27. The method of claim 26, wherein the circulatory disorder is hypertension, ischemia, vasopasms or angina pectoris.

28. The method of claim 20, wherein Z is —O—.

29. The method of claim 21, wherein $R^6$ is lower-alkoxy and $R^7$, $R^8$ and $R^9$ are hydrogen.

30. The method of claim 21, wherein $R^6$ and $R^8$ are hydrogen, $R^7$ is lower-alkoxy and $R^9$ is halogen.

31. The method of claim 20, wherein $R^4$ is hydrogen, 2-pyrimidinyl, 2- or 3-furyl, 2- or 3-thienyl, morpholino or p-methoxyphenyl.

32. A compound of the formula

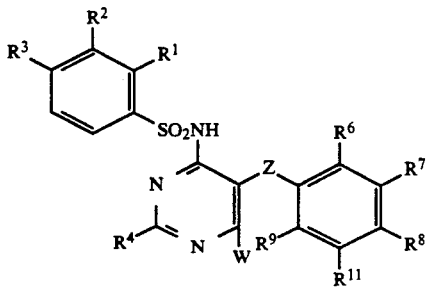

wherein
R[1] is hydrogen;
R[2] is hydrogen;
R[3] is lower alkyl;
R[4] is hydrogen, lower-alkyl, 2-thienyl, 3-thienyl or 3-furyl;
R[6] is lower-alkoxy;
R[7] to R[9] are hydrogen;
R[11] is halogen
Z is —O—
W is 1,3-dioxolan-4-ylmethoxy, 2,2-dimethyl-1,3-dioxolan-4-ylmethoxy or 2,3-dihydroxy-propoxy
or a stereiosomer or salt thereof.

33. A compound according to claim 32 selected from the group consisting of:
(S)-4-tert-butyl-N-[6-(2,2-dimethyl-1,3-dioxolan-4-ylmethoxy)-5-(2-methoxy-phenoxy)-2-methyl-pyrimidin-4-yl]-benzenesulfonamide,
(R)-4-tert-butyl-N-[6-(2,3-dihydroxy-propoxy-5-(2-methoxy-phenoxy)-2-methyl-6-(2-pyrimidin-4-yl]-benzenesulfonamide,
(R)-4-tert-butyl-N-[5-(5-fluoro-2-methoxy-phenoxy)-6-(2,2-dimethyl-1,3-dioxolan-4-ylmethoxy)-pyrimidin-4-yl]-benzenesulfonamide,
(S)-4-tert-butyl-N-[5-(5-fluoro-2-methoxy-phenoxy)-6-(2,2-dimethyl-1,3-dioxolan-4-ylmethoxy)-pyrimidin-4-yl]-benzenesulfonamide,
(R)-4-tert-butyl-N-(5-fluoro-2-methoxy-phenoxy)-6-(2,3-dihydroxy-propoxy-pyrimidin-4-yl]-benzenesulfonamide,
4-tert-butyl-N-[6-[(S)-1,3-dioxolan-4-ylmethoxy]-5-(2-methoxy-phenoxy)-2-(thiophen-2-yl)-pyrimidin-4-yl]-benzenesulfonamide,
(R)-4-tert-butyl-N-[6-(2,3-dihydroxy-propoxy)-5-(2-methoxy-phenoxy)-2-(thiophen-2-yl)-pyrimidin-4-yl]-benzenesulfonamide,
4-tert-butyl-N-[6-(R)-1,3-dioxolan-4-lymethoxy]-5-(2-methoxy-phenoxy)-2-(thiophen-2-yl)-pyrimidin-4-yl]-benzenesulfonamide,
(S)-4-tert-butyl-N-[6-(2,3-dihydroxy-propoxy)-5-(2-methoxy-phenoxy)-2-(thiophen-2-yl)-pyrimidin-4-yl]-benzenesulfonamide,
(R)-4-tert-butyl-N-[6-(2,2-dimethyl-1,3-dioxolan-4-ylmethoxy)-5-(2-methoxy-phenoxy)-2-(thiophen-3-yl)-pyrimidin-4-yl]-benzenesulfonamide,
4-tert-butyl-N-[6-[(S)-2,3-dihydroxy-propoxy]-5-(2-methoxy-phenoxy)-2-(thiophen-3-yl)-pyrimidin-4-yl]-benzenesulfonamide,
(S)-4-tert-butyl-N-[(2,2-dimethyl-1,3-dioxolan-4-ylmethoxy)-5-(2-methoxy-phenoxy)-2-(thiophen-3-yl)-pyrimidin-4-yl]-benzenesulfonamide,
4-tert-butyl-N-[6-[(R)-2,3-dihydroxy-propoxy]-5-(2-methoxy-phenoxy)-2-(thiophen-3-yl)-pyrimidin-4-yl]-benzenesulfonamide,
(S)-4-tert-butyl-N-[6-(2,2-dimethyl-1,3-dioxolan-4-ylmethoxy)-2-(furan-3-yl)-5-(2-methoxy-phenoxy)-pyrimidin-4-yl]-benzenesulfonamide,
(R)-4-tert-butyl-N-[2-(furan-3-yl)-6-(2,3-dihydroxy-propoxy)-5-(2-methoxy-phenoxy)-pyrimidin-4-yl]-benzenesulfonamide,
(R)-4-tert-butyl-N-[6-(2,2-dimethyl-1,3-dioxolan-4-ylmethoxy)-2-(furan-3-yl)-5-(2-methoxy-phenoxy)-pyrimidin-4-yl]-benzenesulfonamide; and
(S)-4-tert-butyl-N-[2-(furan-3-yl)-6-(2,3-dihydroxy-propoxy)-5-(2-methoxy-phenoxy)-pyrimidin-4-yl]-benzenesulfonamide.

* * * * *